US008863594B2

(12) United States Patent
Taylor et al.

(10) Patent No.: US 8,863,594 B2
(45) Date of Patent: Oct. 21, 2014

(54) SAMPLE CONTAINER AND FILTRATION APPARATUS AND METHOD OF FILTRATION USING SAME

(71) Applicant: Roush Life Sciences, LLC, Livonia, MI (US)

(72) Inventors: Thomas Taylor, Windham, NH (US); Jeffrey Kane, Worcester, MA (US); George W. Jordan, Worcester, MA (US)

(73) Assignee: Foxx Life Sciences, Salem, NH (US)

( * ) Notice: Subject to any disclaimer, the term of this patent is extended or adjusted under 35 U.S.C. 154(b) by 0 days.

(21) Appl. No.: 13/658,425

(22) Filed: Oct. 23, 2012

(65) Prior Publication Data

US 2013/0139617 A1    Jun. 6, 2013

Related U.S. Application Data

(63) Continuation-in-part of application No. 12/070,974, filed on Feb. 22, 2008.

(51) Int. Cl.
*B01L 3/00*         (2006.01)
*G01N 1/14*         (2006.01)
*G01N 1/34*         (2006.01)
*G01N 1/40*         (2006.01)
*C12M 1/00*         (2006.01)
*G01N 1/22*         (2006.01)

(52) U.S. Cl.
CPC ........... *G01N 1/34* (2013.01); *B01L 2400/0633* (2013.01); *B01L 3/502738* (2013.01);
(Continued)

(58) Field of Classification Search
CPC ................ B01L 3/50825; B01L 2400/0633; B01L 2400/0655; B01L 2400/0681; B01L 2300/049; B01L 3/502738; B01L 3/567
See application file for complete search history.

(56) References Cited

U.S. PATENT DOCUMENTS 5,785,044 A  *  7/1998  Meador et al. ................ 600/573
5,792,425 A       8/1998  Clark et al. .................... 422/101
(Continued)

FOREIGN PATENT DOCUMENTS

| EP | 0 838 253 A2 | 4/1998 | ........... B01D 29/085 |
| JP | 10-211403 A  | 8/1998 | ............. B01D 29/01 |
| JP | 11-179238 A  | 7/1999 | ............... B04B 5/02 |

OTHER PUBLICATIONS

Korean Intellectual Property Office, International Search Report—Application No. PCT/US2009/034855, dated Aug. 31, 2009 (4 pages), including the Written Opinion of the International Searching Authority.

*Primary Examiner* — Dirk Bass
*Assistant Examiner* — Jennifer Wecker
(74) *Attorney, Agent, or Firm* — Sunstein Kann Murphy & Timbers LLP

(57) ABSTRACT

A sample container and filtration apparatus includes a sample container portion with an interior volume and a fluid path passing through a bottom wall. The sample container may also include a valve casing connected to and moveable relative to the sample collection portion between a first and second position. A valve secured to and moveable with the valve casing may close the fluid path of the sample collection portion when in a first position and open the fluid path when in a second position. The apparatus may also include a vacuum base coupling portion that is distal to the valve casing, and includes a filter membrane support surface for supporting a filter membrane.

17 Claims, 34 Drawing Sheets

(52) U.S. Cl.
CPC ............. *B01L 3/567* (2013.01); *B01L 3/50825* (2013.01); *G01N 1/4077* (2013.01); *B01L 2200/08* (2013.01); *B01L 2200/141* (2013.01); *B01L 2300/046* (2013.01); *B01L 2300/0681* (2013.01); *B01L 2300/0832* (2013.01); *G01N 2001/4088* (2013.01); B01L 3/502 (2013.01); *B01L 2300/043* (2013.01); *B01L 2300/049* (2013.01)

USPC ....... 73/863.23; 73/864.61; 422/50; 600/573; 435/283.1

(56) References Cited

U.S. PATENT DOCUMENTS

| | | | |
|---|---|---|---|
| 5,899,349 A | 5/1999 | Moore | 215/277 |
| 6,277,646 B1 | 8/2001 | Guirguis et al. | 436/165 |
| 6,726,879 B2 | 4/2004 | Ng et al. | 422/58 |
| 7,270,959 B2 | 9/2007 | Hudak | 435/7.1 |
| 7,686,771 B2 | 3/2010 | Watts et al. | 600/573 |
| 2003/0190259 A1* | 10/2003 | Alley | 422/58 |
| 2007/0134134 A1* | 6/2007 | Watts et al. | 422/102 |
| 2007/0144959 A1* | 6/2007 | Zuk | 210/473 |
| 2007/0267426 A1* | 11/2007 | Arciniegas et al. | 220/756 |

* cited by examiner

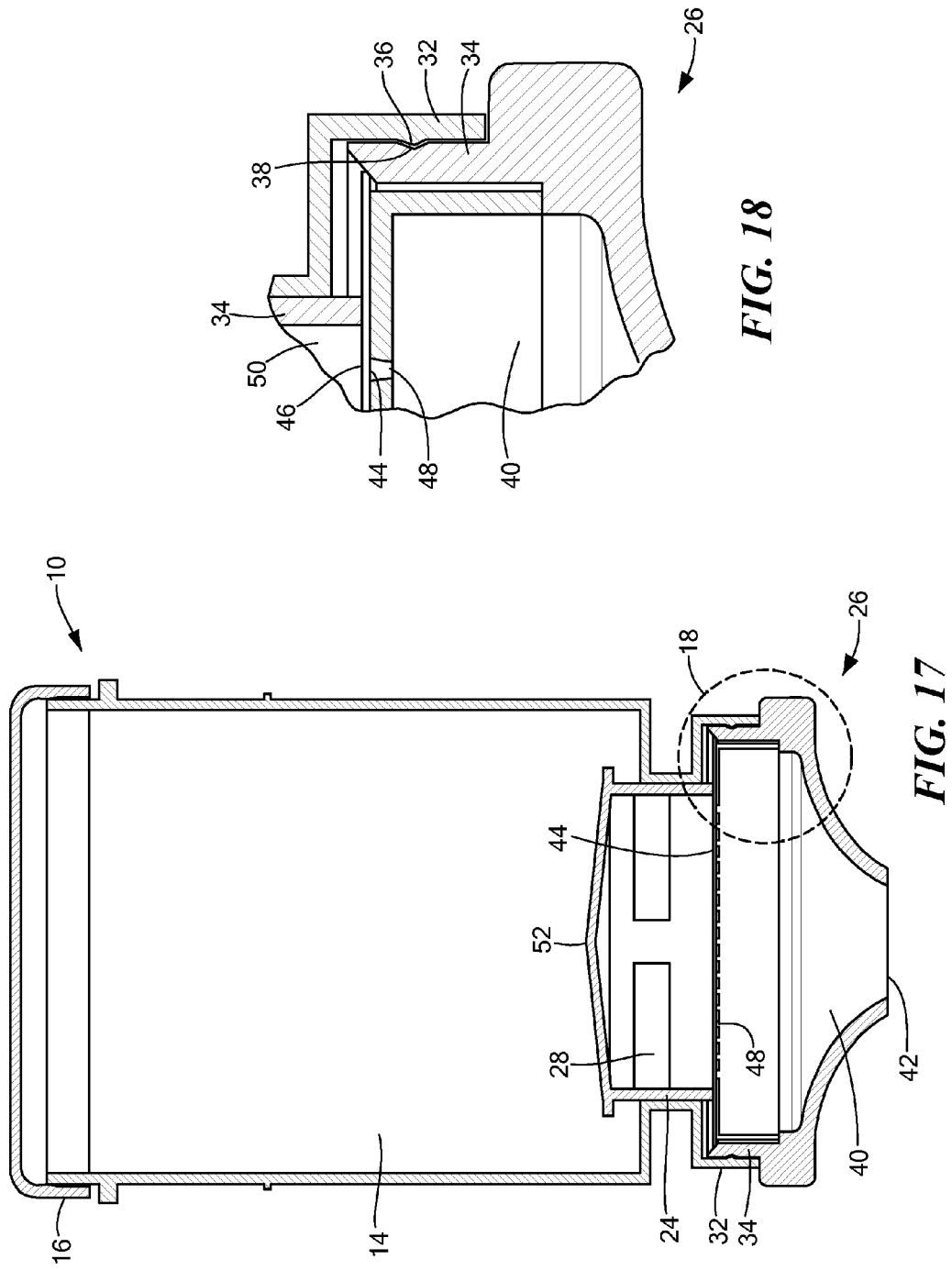

SAMPLE CONTAINER AND FILTRATION APPARATUS AND METHOD OF FILTRATION USING SAME

PRIORITY

This application is a continuation in part of co-pending U.S. patent application Ser. No. 12/070,974, entitled "Sample Container and Filtration Apparatus and Method of Filtration Using Same," filed Feb. 22, 2008, and naming Jeffrey Kane, Thomas Taylor, Christopher M. Catinella, and Ryan Neil Peter Hall as inventors, the disclosure of which is incorporated herein, in its entirety, by reference.

TECHNICAL FIELD

The present invention relates to sample filtration, and more particularly to containers for collecting samples and filtering the collected samples.

BACKGROUND ART

A traditional form of sample testing, in particular water testing, utilizes a vacuum filtration system to pull the sample through a membrane for further culturing and analysis. The system uses a sample container for collecting and transporting the sample to a testing site and a vacuum base that is configured to attach to a vacuum manifold source. With reference to Prior Art FIGS. 1-2, a filter membrane is removed from sterile packaging (e.g., by opening the packaging and grabbing the membrane with metal forceps that have been flamed) and is placed on the vacuum base. A vacuum funnel is clamped thereover to secure the assembly prior to vacuum filtration of the sample.

In ideal practice, the funnel and the base are autoclaved overnight prior to use (Prior Art FIG. 3). A sample bottle is taken from storage and transported to a site of interest. Some amount of sample (e.g., 250 milliliters (ml) of water) is placed in the sample container. The sample container is labeled and placed in a cooler for transport to the lab, and the sample is placed in a refrigerator at the lab until testing (Prior Art FIG. 4).

When the test environment is ready, the sample container is removed from the refrigerator (Prior Art FIG. 5). The sample container is opened, and a specified amount of sample (e.g., 100 ml) is poured into the funnel of the assembly (see Prior Art FIG. 6). The vacuum source is turned on via the manifold, and within 10 to 30 seconds, the filtrate is pulled through the membrane (Prior Art FIG. 7).

After vacuum filtration, the vacuum source is turned off, the funnel and the clamp are removed and placed aside (Prior Art FIG. 8). The forceps are flamed and extinguished. The filter is removed from the base with the forceps and placed in a Petri dish (Prior Art FIG. 9).

Subsequent to removing the filter, the filter and base are rinsed with distilled or filtered water (Prior Art FIG. 10), the funnel and base assembly are clamped together and are put in a Ultraviolet (UV) chamber for a period of time (e.g., five minutes) (Prior Art FIG. 11). The assembly is placed back on the manifold (Prior Art FIG. 12), the clamp and funnel are removed, and the base is flamed for a period of time (e.g., 10 to 15 seconds) (Prior Art FIG. 13). The interior of the funnel is also flamed for a period of time (e.g., 10 to 15 seconds) (Prior Art FIG. 14), and the assembly is clamped back together for the next sample testing (Prior Art FIG. 15).

As was noted above, the above steps are the recommended, ideal steps for ensuring that sample contamination is at a minimum. However, in practice, not all of the steps are typically performed, and sample contamination remains a problem with regard to the majority of the above iterated steps. The prior art would greatly benefit from solutions that would reduce or eliminate sample contamination with regard to one or more of the above described sample testing steps.

SUMMARY OF THE EMBODIMENTS

The above described and other disadvantages of the prior art are overcome and alleviated by various embodiments presently described sample container and filtration apparatus, which comprises a sealable sample container and a surface that is configured to interface with a vacuum base. When the surface interfaces with the vacuum base, a portion of the sample container is broached, providing a pathway for the vacuum source to pull the sample therethrough.

In an exemplary embodiment, the broachable portion of the sample container comprises an actuating valve. When the sample container is placed onto the base, the valve opens due to interaction between the valve and the base, and a pathway opens between the sample and the base.

In exemplary embodiments, a lower portion of the valve contacts an upper portion of the base during the mating of the sample container and the base. The valve is pressed upwardly into the sample container, and at least one pathway is opened thereby.

In other exemplary embodiments, a plurality of pathways are opened around the valve to more evenly distribute the sample across a filter, which is situated between the valve and the vacuum source.

In other exemplary embodiments, the interface provides an audible signal and/or provides a ridge or projection in groove interface for positive engagement between the sample container and the base.

The method for using the sample container and filtration apparatus significantly reduces the possibility of contamination of the sample and during the sample testing procedure relative to the conventional devices and procedures, provides more consistent and reliable test results, and significantly reduces the number of preparation and testing steps for the testing procedure.

In accordance with additional embodiments, a sample container may have a sample collection portion, a valve casing, and a valve. The sample collection portion may have at least one wall defining an interior volume of the sample container, and an outlet passing through a bottom wall. The valve casing may be moveably connected to the sample collection portion (e.g., in a telescopic manner), such that the sample container and valve casing are moveable relative to one another between a first position and a second position. The valve casing may form a vacuum base coupling portion. The valve (e.g., a plug valve) may be secured to and moveable with the valve casing. The valve may close the outlet of the sample collection portion when in the first position, and extend into the interior volume of the sample container when in the second position. The valve may also be configured to open a pathway between the interior volume of the sample collection portion and an exterior when in the second position.

In some embodiments, the sample container may also include a locking mechanism located between the sample container portion and the valve casing. The locking mechanism may prevent the relative movement between the sample collection portion and the valve casing. For example, the locking mechanism may include a peel strip that is removable from the sample container to allow the relative movement between the sample collection portion and the valve casing. The peel strip may include a peel tab.

The sample collection portion may also include a skirt that extends distally from the bottom surface of the sample collection portion, and the valve casing may include a proximally extending wall that defines a recess within the valve casing. The skirt may extend into the recess. The proximally extending wall may include a plurality of protrusions extending inward from the proximally extending wall, and the skirt may include a plurality of indentations. The protrusions may extend into the indentations to lock the sample collection portion to the valve casing. Additionally or alternatively, the skirt may include a plurality of protrusions extending out from the skirt, and the proximally extending wall may include a plurality of indentations. The protrusions may extend into the indentations to lock the sample collection portion to the valve casing.

The sample container may also include a cover with a tamper evident latch, and/or a bottom cap configured to fit over the bottom of the valve casing. The bottom cap may also include a tamper evident latch. Additionally or alternatively, the sample container may include a seal covering at least a portion of a bottom surface of the valve casing. The sample container may also include a vacuum base connectable with the vacuum base coupling portion, and including a filter support surface for supporting a filter membrane.

In accordance with further embodiments a method of filtering a fluid sample may include receiving a sample for filtration within a sample collection portion of a sample container. The sample container may also have a valve casing moveably connected to the sample collection portion (e.g., in a telescopic manner), and a valve (e.g., a plug valve) secured to and moveable with the valve casing. The sample collection portion may have at least one wall defining an interior volume of the sample container and an outlet passing through a bottom wall.

The method may also include mating the valve casing of the sample container with a vacuum filtration base, and moving the sample collection portion of the sample container relative to the valve casing. The vacuum filtration base may have a support surface that supports a filter membrane for filtering the collected sample. The relative movement may cause the valve to transition from a first position in which the valve closes the outlet toward a second position in which the outlet is open to allow fluid to pass through the outlet. The method may then apply a vacuum to the sample container to draw the collected sample from the sample collection portion, through the outlet, and through the filter to filter the collected sample. After filtering, the method may remove the sample container from the vacuum filtration base, and remove the filter membrane from the filter membrane support surface.

In some embodiments, the method may also include removing a locking mechanism located between the sample container portion and the valve casing. Removing the locking mechanism may allow the relative movement between the sample collection portion and the valve casing. The locking mechanism may include a peel strip that is removable from the sample container to allow the relative movement between the sample collection portion and the valve casing. The peel strip may include a peel tab.

The method may also include collecting the sample for filtration within the sample collection portion, and placing a top cover over a top opening of the sample collection portion after collecting the fluid sample to close the top opening of the sample collection portion. In such embodiments, the method may also include removing the top cover after moving the sample collection portion of the sample container relative to the valve casing. The top cover may be secured to the sample collection portion with a tamper evident locking mechanism, and removing the top cover may include breaking the tamper evident locking mechanism.

In further embodiments, the method may also include removing a bottom cap located on a bottom surface of the valve casing prior to mating the valve casing with the vacuum filtration base. Additionally, the plug member may extend into the interior volume of the sample collection portion in the second position to open the outlet. Moving the sample collection portion relative to the valve casing may include moving the sample collection portion relative to the valve casing in a telescopic manner.

In accordance with further embodiments, a sample container and filtration apparatus may include a sample collection portion, a valve casing, a valve, a vacuum base, and a filter membrane. The sample collection portion may have at least one wall defining an interior volume of the sample container, and a fluid path passing through a bottom wall. The valve casing may be moveably connected to the sample collection portion (e.g., in a telescopic manner), and the sample container and valve casing may be moveable relative to one another between a first position and a second position. The valve may be secured to and moveable with the valve casing, and may close the fluid path of the sample collection portion when in the first position and open the fluid path when in the second position. The vacuum base coupling portion may be distal to the valve casing, and may include a filter membrane support surface. The filter membrane may be supported by the filter membrane support surface, and may filter a sample collected within the sample collection portion.

Further embodiments may include a locking mechanism located between the sample container portion and the valve casing. The locking mechanism may prevent the relative movement between the sample collection portion and the valve casing. The locking mechanism may include a peel strip that is removable from the sample container to allow the relative movement between the sample collection portion and the valve casing. The peel strip may include a peel tab.

The sample collection portion may include a skirt extending distally from the bottom surface of the sample collection portion, and the valve casing may include a proximally extending wall defining a recess within the valve casing. The skirt may extend into the recess. The proximally extending wall may include a plurality of protrusions extending inward from the proximally extending wall, and the skirt may include a plurality of indentations. The protrusions may extend into the indentations to lock the sample collection portion to the valve casing. Additionally or alternatively, the skirt may include a plurality of protrusions extending out from the skirt, and the proximally extending wall may include a plurality of indentations. The protrusions may extend into the indentations to lock the sample collection portion to the valve casing.

In some embodiments, the sample container and filtration apparatus may include a cover with a tamper evident latch, and a bottom cap configured to fit over a bottom of the vacuum base coupling portion and including a tamper evident latch. The valve casing may have an annular surface that contacts an upper surface of the filter membrane, and the annular surface may seal against the upper surface of the filter membrane. The vacuum base coupling portion may include an outlet downstream of the filter membrane that passes through the filter membrane support surface. The filter membrane support surface may include a plurality of filter support ribs and a plurality of channels. The plurality of filter support ribs may support the filter membrane, and the plurality of channels may channel fluid passing through the filter to the outlet of the sample container and filtering apparatus. The vacuum base coupling portion may include at least one protrusion configured to interact with the vacuum base to secure the sample container to the vacuum base. The filter membrane may be distal to the fluid path.

In accordance with additional embodiments, a method of filtering a fluid sample may include receiving a sample for filtration within a sample collection portion of a sample container and filtration apparatus. The sample collection portion may have at least one wall defining an interior volume of the sample container and a fluid path passing through a bottom surface. The sample container and filtration apparatus may also include a valve casing, a valve, a vacuum base coupling portion and a filter membrane. The valve casing may be moveably connected to the sample collection portion (e.g., in a telescopic manner), and the valve may be secured to and moveable with the valve casing. The vacuum base coupling portion may be distal to the valve casing, and the coupling portion may include a filter membrane support surface. The filter membrane may be located distal to the fluid path and may be supported by the filter membrane support surface. The filter membrane may filter a sample collected within the sample collection portion.

The method may also include (1) mating the coupling portion with a vacuum filtration base, (2) moving the sample collection portion relative to the valve casing, (3) applying a vacuum to the sample container and filtration apparatus to draw the collected sample from the sample collection portion, through the fluid path, and through the filter to filter the collected sample, (4) removing the sample collection portion and the valve casing from the coupling portion, and (5) removing the filter membrane from the filter membrane support surface. The relative movement may cause the valve to transition from a first position in which the plug valve closes the fluid path toward a second position in which the fluid path is open to allow fluid to pass through the fluid path.

The method may also include removing a locking mechanism located between the sample container portion and the valve casing to allow the relative movement between the sample collection portion and the valve casing. The locking mechanism may include a peel strip that is removable from the sample container to allow the relative movement between the sample collection portion and the valve casing. The peel strip may include a peel tab.

In some embodiments, the method may also include collecting the sample for filtration within the sample collection portion, and placing a top cover over a top opening of the sample collection portion after collecting the fluid sample (e.g., to close the top opening of the sample collection portion). The method may also remove the top cover after moving the sample collection portion of the sample container relative to the valve casing. The top cover may be secured to the sample collection portion with a tamper evident locking mechanism, and removing the top cover may include breaking the tamper evident locking mechanism.

The method may also include removing a bottom cap located on a bottom surface of the valve casing prior to mating the valve casing with the vacuum filtration base. The bottom cap may include a tamper evident latch. The valve may extend into the interior volume of the sample collection portion in the second position. The valve may be a plug valve, and moving the sample collection portion relative to the valve casing may include moving the sample collection portion relative to the valve casing in a telescopic manner.

BRIEF DESCRIPTION OF THE DRAWINGS

The foregoing features of embodiments will be more readily understood by reference to the following detailed description, taken with reference to the accompanying drawings, in which:

PRIOR ART

PRIOR ART

PRIOR ART

PRIOR ART

PRIOR ART

PRIOR ART

PRIOR ART

PRIOR ART

PRIOR ART

PRIOR ART

PRIOR ART

PRIOR ART

PRIOR ART

PRIOR ART

PRIOR ART

FIG. 17 is a cross sectional view of an exemplary sample container and filtration apparatus mated with an exemplary base;

FIG. 18 is a partial close-up view of the mating of the exemplary sample container and filtration apparatus and the exemplary base.

DETAILED DESCRIPTION OF SPECIFIC EMBODIMENTS

Reference will now be made in detail to exemplary embodiments, examples of which are illustrated by the accompanying drawings. As indicated above, various embodiments described herein may include a broachable surface during the interface of the sample container and a base that is configured to be connected to a vacuum source.

As will be understood from the above and from the following detailed description, various embodiments of the sample container and filtration apparatus significantly reduce the possibility of contamination of the sample and during the sample testing procedure relative to the conventional devices and procedures. The presently described apparatus provides more consistent and reliable test results. The presently described apparatus also significantly reduces the number of preparation and testing steps for the testing procedure.

Figure 16:
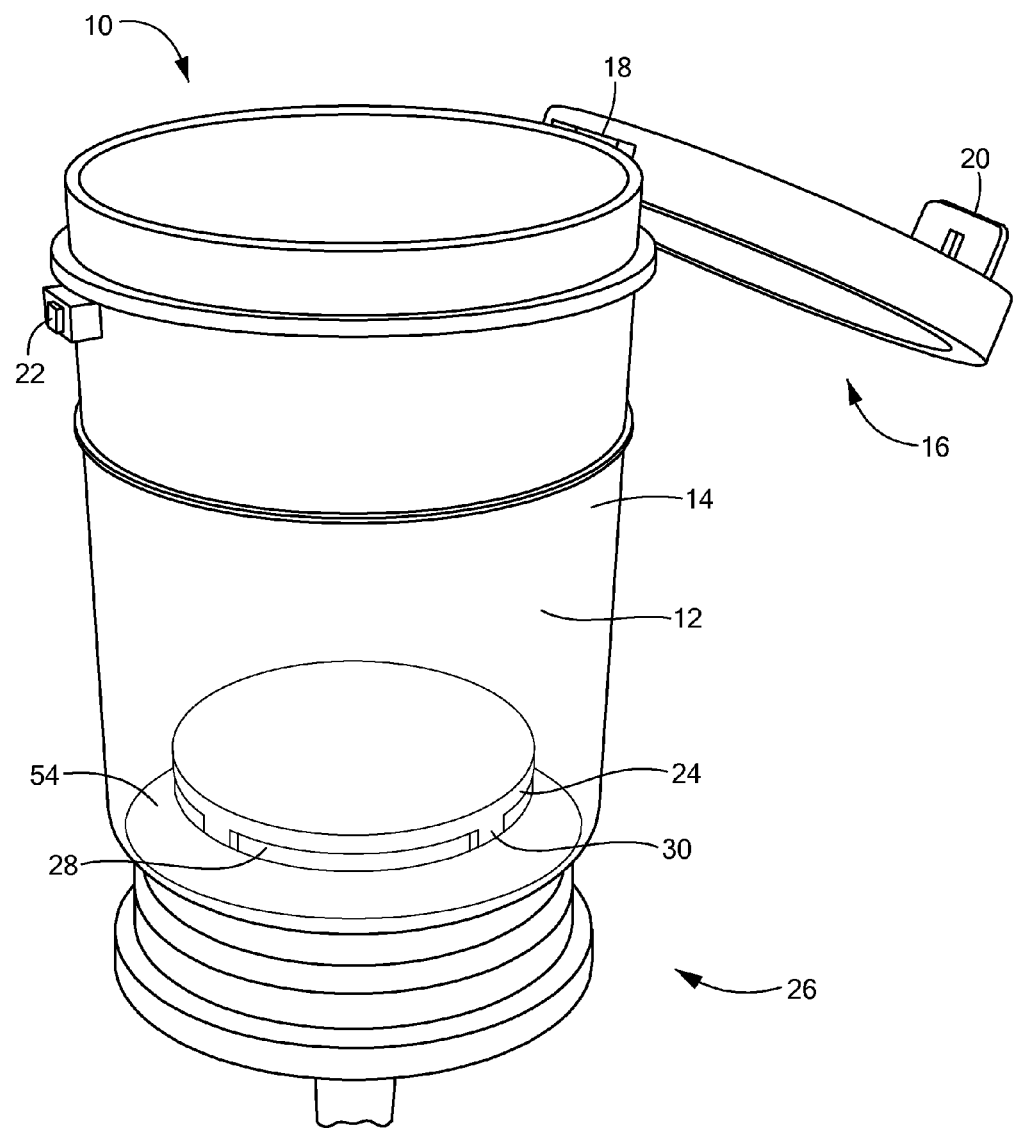
FIG. 16 is a perspective view of an exemplary sample container and filtration apparatus.

Referring now to FIG. 16, an exemplary sample container and filtration apparatus (hereinafter referred to simply as "sample container") is illustrated generally at 10. The sample container includes an interior volume 12 configured to receive a predetermined amount of sample (e.g., 100 ml, 200 ml, or 250 ml, among others). In exemplary embodiments, a recommended level of sample is indicated by a fill line 14.

The exemplary sample container also includes a cover 16, illustrated in this exemplary embodiment as a cap with a living hinge 18 (although other embodiments are contemplated herein, including without limitation, threaded covers, etc.). In exemplary embodiments, the sample container is transported to a sample site, removed from a sterile container (e.g., sterile flexible packaging), and a sample amount is placed within the interior volume 14. The cover 16 is then closed to seal the sample therein. The cover 16 may interface with a complementary container surface in such a way to reduce the possibility of accidental re-opening, e.g., with a friction fit configuration, with a ridge or projection in groove configuration, with a locking configuration, etc.

In exemplary embodiments, the cover includes a locking member 20 that positively engages a projection 22 on the sample container. This tab may be pliable to permit re-opening of the cover, or the tab may be configured to break in order to re-open the cover. A breakable tab 20 provides benefit in serving as a positive indication that the sample has not been exposed to possible sources of contamination between the sample site and the testing site. During testing and just prior to applying vacuum, the tab may be broken to allow the cap to be opened such that a vacuum may be better drawn through the sample container. In the alternative, one or more vents (not shown) may be provided in the cover or on another surface of the sample container to better facilitate application of the vacuum.

The sample container 10 also includes a broachable portion 24. When the sample container is interfaced with a base that is configured to interface with a vacuum source, shown generally at 26, the broachable portion 24 exposes a pathway 28 between the interior volume 14 and the vacuum source.

In the illustrated exemplary embodiment, the broachable surface 24 comprises a sliding valve that is actuated into the interior volume 14 of the sample container 10 during mating of the sample container and the base. That is, as the sample container 10 is pressed over the base, an interface portion 30 of the sliding valve contacts the base 26 and forces the sliding valve to move into the interior volume exposing the pathway 28. While the following describes, as an exemplary embodiment, a sliding valve having vents, it should be recognized that the present invention is not limited thereto, but instead contemplates other forms of broachable surfaces as well. Thus, the following (with regard to the sliding valve, the vents or otherwise) should be read as being exemplary rather than limiting.

In exemplary embodiments, a plurality of pathways 28 is exposed. In the illustrated exemplary embodiment, the plurality of pathways 28 present as vents that are evenly spaced around the circumferential periphery of the valve. Providing vents around portions of the circumferential periphery of the valve allows sample to be more evenly distributed over a filter that is provided between the valve and the vacuum source.

Referring now to FIG. 17, an exemplary embodiment is illustrated that elaborates on an interface between the sample container and the base. As before, the illustrated exemplary embodiment includes a cover 16, an interior volume 14 and a sliding valve 24. With additional reference to FIG. 18, the illustrated exemplary sample container 16 includes an interface surface 32 that is complementary to a base interface surface 34. This interface may be a friction fit, a stacking fit with supplemental mechanisms for preventing accidental disassociation of the interface (e.g., via magnets provided in or near the interface surfaces 32, 34), or, as illustrated, an interface that includes a ridge 36 in groove 38 (or the like, such as a projection in groove or projection in hole) configuration. In the case of the ridge in groove configuration or the like, the interface may be configured to generate an audible and/or tactile feedback indicative of positive mating.

Referring still to FIGS. 17 and 18, the illustrated exemplary base element comprises an interior volume 40, a vacuum source pathway 42, and a filter support surface 44, which provides support for a filter 46 and exposes the filter to the vacuum source. In the illustrated embodiment, the filter support surface includes a plurality of perforations 48.

The exemplary valve is shown in the installed state, with vents 28 exposed to the interior volume 14 of the sample container 10 through interaction with the base 26 during mating of the sample container and the base. In the installed state, an applied vacuum will draw the sample from the interior volume 14 of the sample container, through the vents 28 into an interior volume 50 of the valve 24, through the filter 44 and into the interior volume 40 of the base 26.

With reference to FIG. 17, the valve is illustrated with a sloped surface portion 52 (in the specific illustration, a conical surface). With reference to FIG. 16, the sample container is illustrated with sloping wall surfaces 54. These exemplary embodiments reduce or eliminate standing sample material at the end of the vacuum filtration process.

Figure 19B:
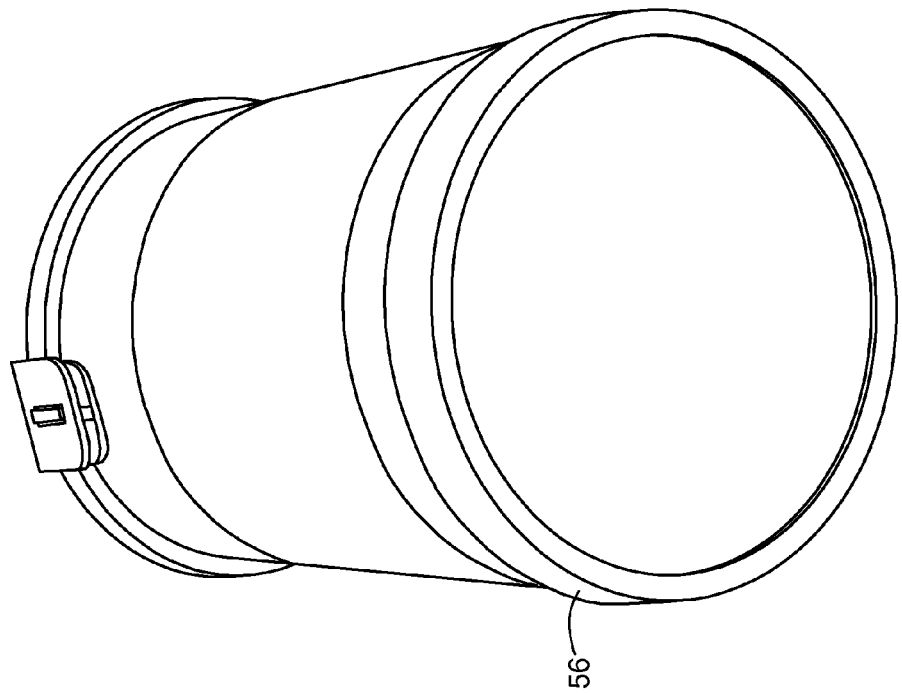
FIGS. 19A and 19B are perspective views of an exemplary sample container and filtration apparatus in an uninstalled state.
Figure 19A:
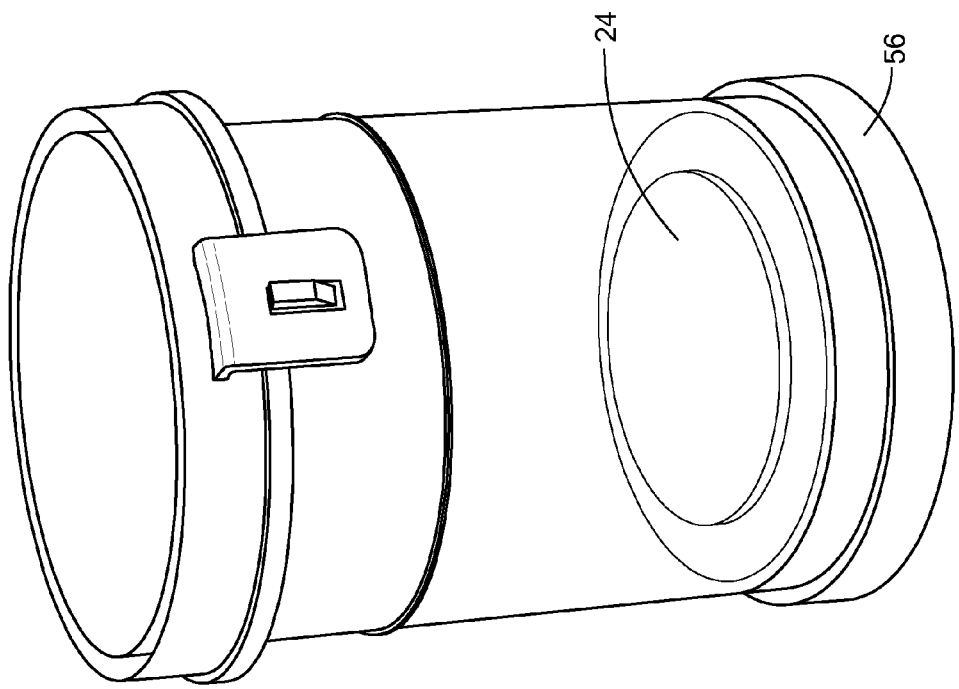

With reference to FIGS. 18 and 19, the sample container may also include a cover 56 provided over the broachable surface 24 to preserve a sterile field prior to testing and/or to prevent accidental broaching of surface 24. It is also noted that FIG. 18 illustrates the broachable surface 24 in an uninstalled state, wherein there is no pathway between the interior volume 14 of the sample container 10 and the exterior of the container.

In exemplary embodiments, the filter may be packaged with the sample container (i.e., between a cover 56 and the broachable surface 24). Alternatively, the filter may be packaged with the base, wherein the filter and the base are maintained in a sterile field (for example, flexible sterile packaging) prior to use. In other embodiments, the filter is separately maintained.

In exemplary embodiments, one or both of the sample container and the base are disposable products. By utilizing the presently described sample container and/or base as disposables, benefit is derived by virtue of the fact that the containers do not need to be cleaned and sterilized between testings. Rather, in the case of the sample container, the sample may simply be collected and tested, without autoclave, rinsing, flaming of surfaces, etc., and then may simply be thrown away in favor of another disposable sample container.

In exemplary embodiments, testing of a sample may easily be done by removing the sample container from sterile packaging (e.g., a sealed sterile bag, or other sealed tamper evident bag) at a sample site, placing sample within the container, sealing the container, and transporting the container directly to the testing site (preferably in a cold environment). The sample container may then be placed on a base, with a filter material between the sample container and the base, a cap or other vent may be opened, and a vacuum source applied through the base. After vacuum filtration is finished, the filter is placed in a culture tray, and one or both of the sample container and base may be thrown away. Thus, in contrast with the above-described prior art method, various embodiments for using the apparatuses described herein significantly reduce the possibility of contamination of the sample and during the sample testing procedure relative to the conventional devices and procedures, provide more consistent and reliable test results, and significantly reduce the number of preparation and testing steps for the testing procedure.

The materials for the sample container and/or base may comprise any convenient material. However, where use as a disposable is desired, inexpensive moldable materials may be preferable. For example, moldable plastics, such as polypropylene or styrene, without limitation, may be used. The sample container may also include or be packaged with materials intended to neutralize chlorinated water, such as sodium theosulfate.

The filter material may be any convenient filter. For example, for coliform, fecal or other biological water testing, standard membrane filters, as are known in the industry, may be used.

Figure 1:
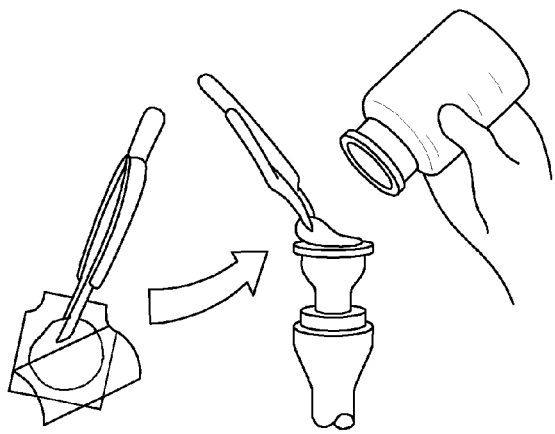
FIG. 1 illustrates a conventional installation of a filter membrane into a vacuum filtration assembly.
Figure 2:
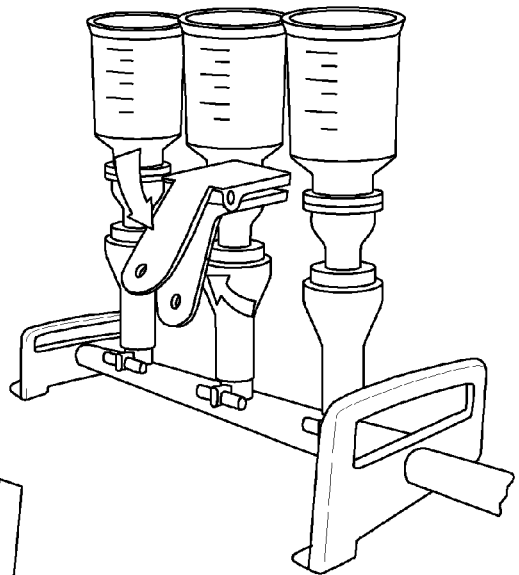
FIG. 2 illustrates a conventional vacuum filtration assembly that is ready for use.
Figure 3:
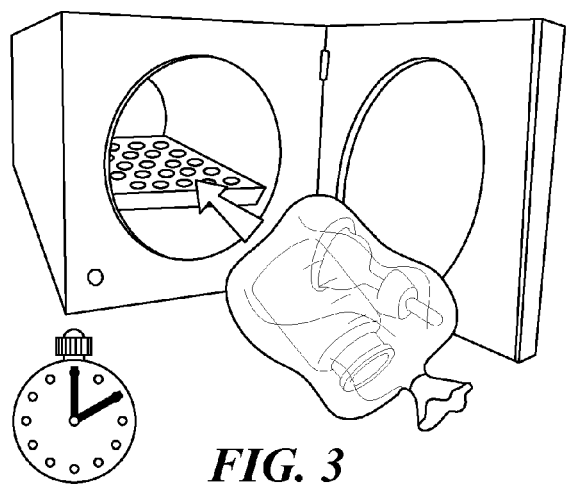
FIG. 3 illustrates the ideal autoclaving of the conventional vacuum funnel and base prior to use.
Figure 4:
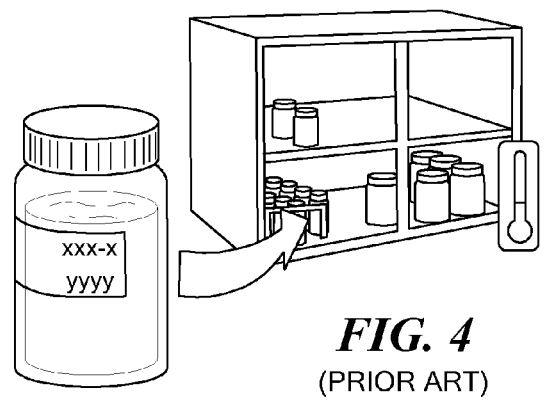
FIG. 4 illustrates a conventional sample container in storage prior to testing.
Figure 5:
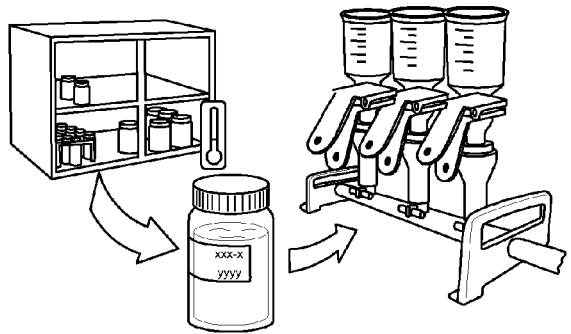
FIG. 5 illustrates conventional transfer of a sample container from storage to the testing assembly.
Figure 6:
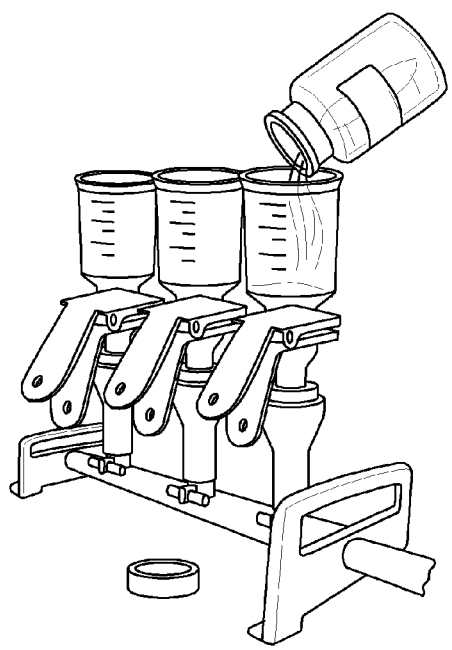
FIG. 6 illustrates conventional transfer of the sample from the sample container into the vacuum funnel.
Figure 7:
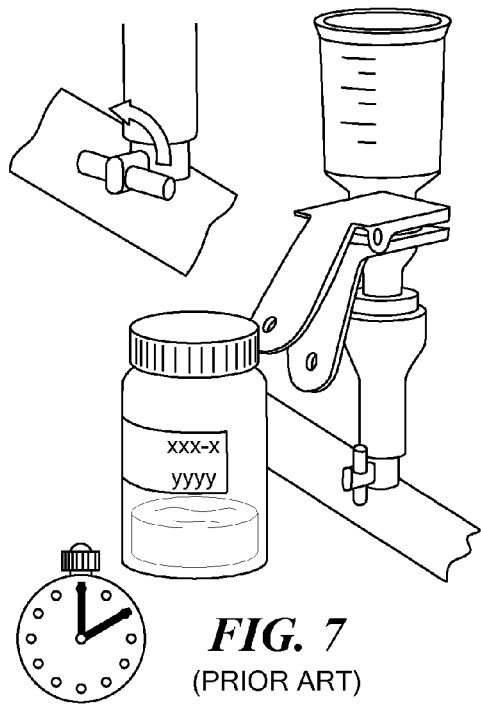
FIG. 7 illustrates conventional vacuum filtration of the sample.
Figure 8:
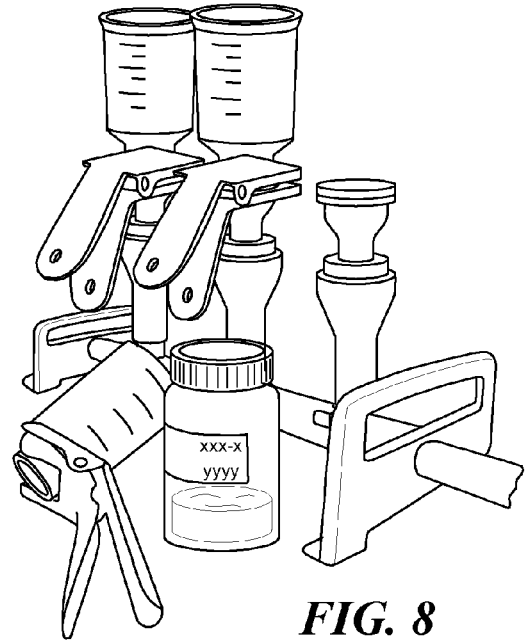
FIG. 8 illustrates removal of the conventional clamp and vacuum funnel.
Figure 9:
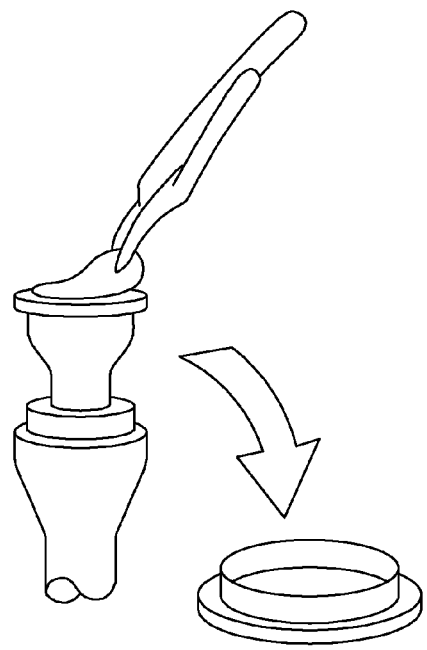
FIG. 9 illustrates transfer of the filter from the conventional base into a Petri dish.
Figure 10:
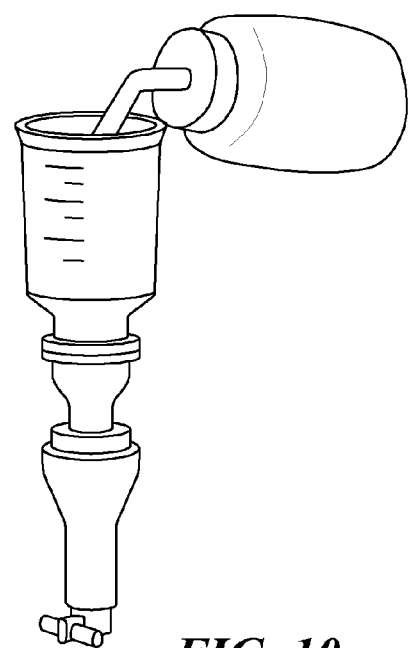
FIG. 10 illustrates conventional rinsing of the funnel and base.
Figure 11:
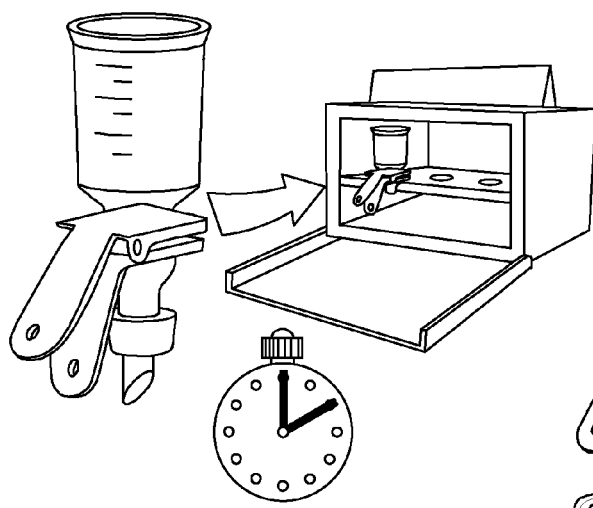
FIG. 11 illustrates conventional UV treatment of the vacuum filtration assembly.
Figure 12:
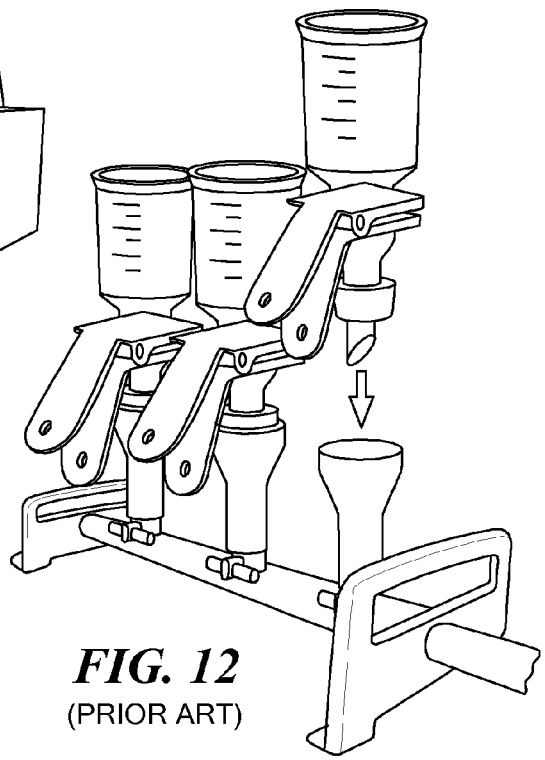
FIG. 12 illustrates conventional re-installation of the vacuum filtration assembly onto the vacuum manifold.
Figure 13:
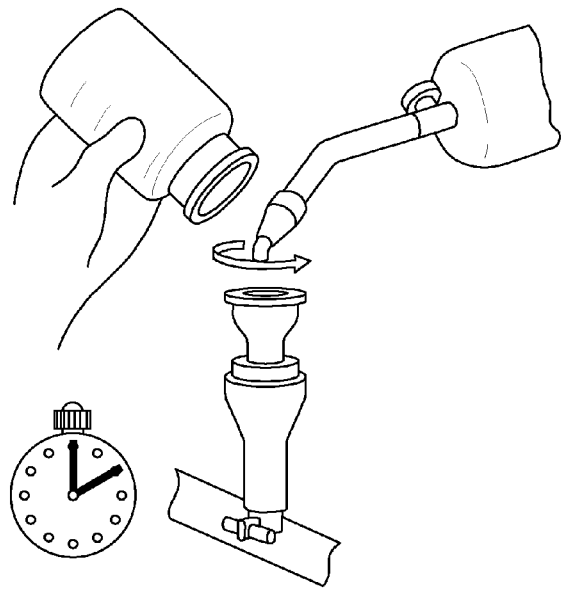
FIG. 13 illustrates conventional removal of the vacuum funnel and flaming of the base.
Figure 14:
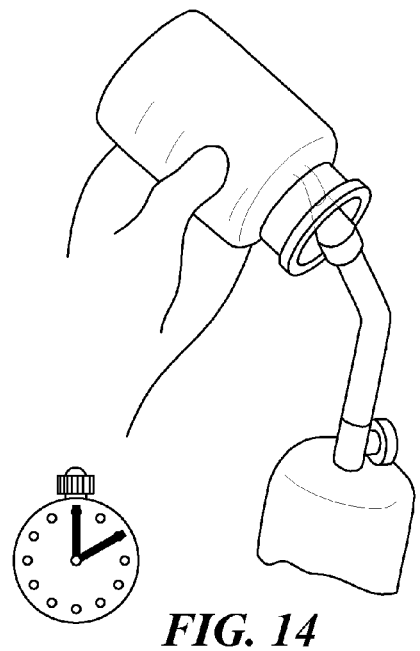
FIG. 14 illustrates conventional flaming of the vacuum funnel.
Figure 15:
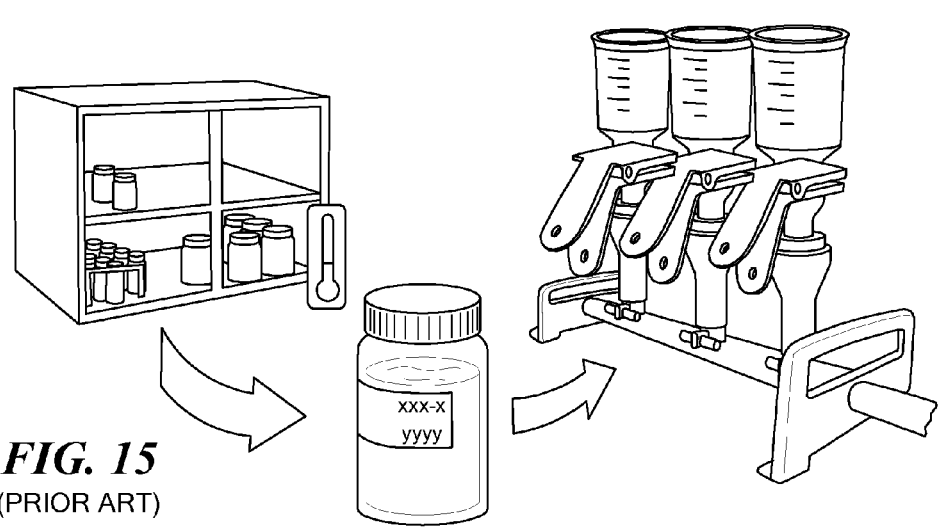
FIG. 15 illustrates the start of a second conventional sample testing with the vacuum filtration assembly.
Figure 20A:
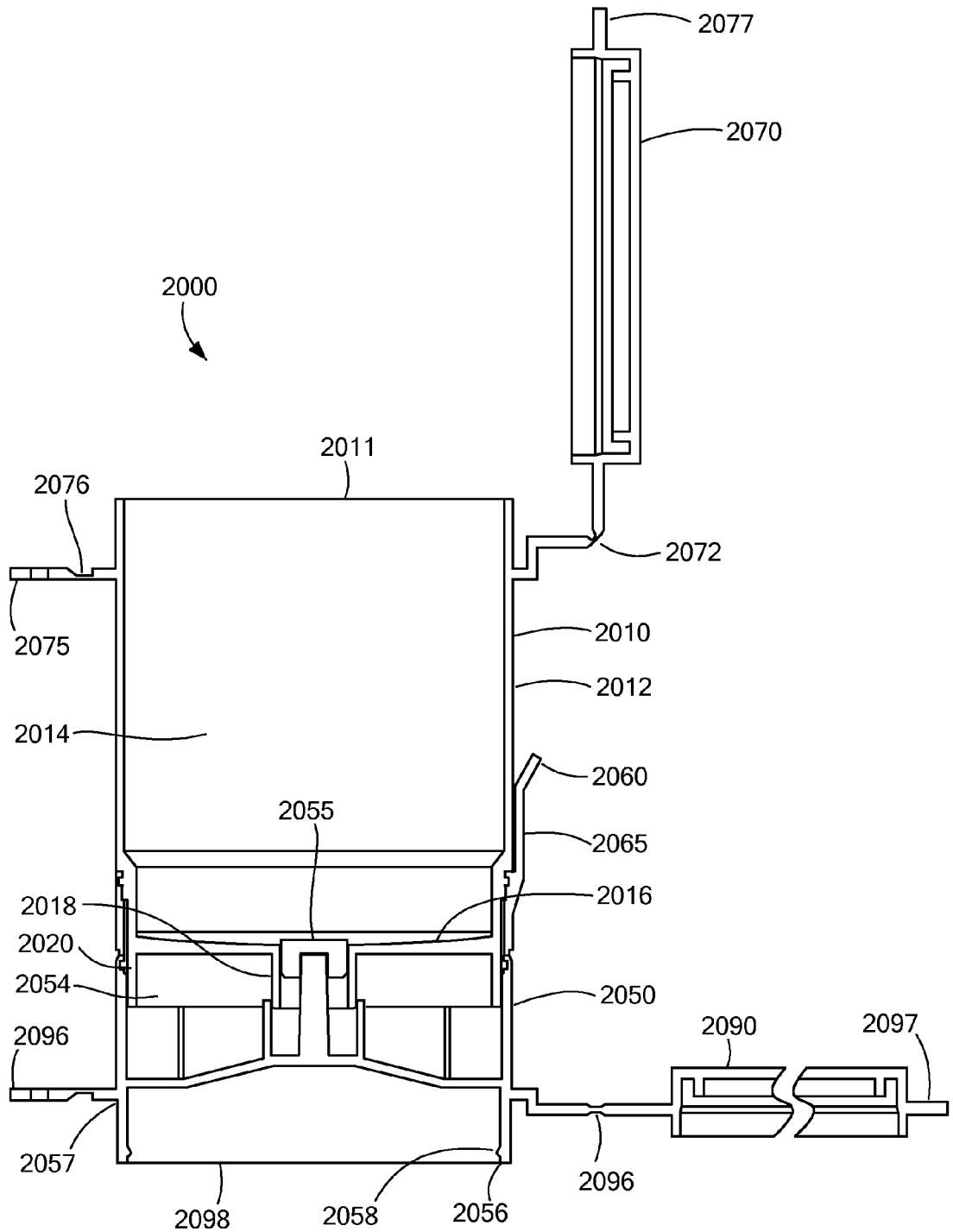
FIG. 20A schematically shows a cross-sectional view of an alternative embodiment of a sample container in the closed mode, in accordance with additional embodiments of the present invention.

As shown in FIGS. 20A and 2B, some embodiments can utilize different actuation to open the fluid path through the sample container. For example, some embodiments may include a sample collection portion 2010 and a valve case 2050. The sample collection portion 2010 may have a wall 2012 that defines an interior volume 2014 in which a user can collect a sample to be filtered. Additionally, the sample collection portion 2010 may also include a bottom wall 2016, and an outlet 2018 extending through the bottom wall 2016 (e.g., so that the sample can be drawn out from the bottom of the sample collection portion 2010).

As the name suggests, the valve case 2050 includes a valve 2055 (e.g., a plug valve) that is secured within valve case 2050. As discussed in greater detail below, the plug valve 2055 is moveable with the valve case 2050 (e.g., relative to the sample collection portion 2010 and is stationary relative to the valve case 2050) to open and close the outlet 2018 of the sample collection portion 2010. Additionally, the bottom of the valve case 2050 can include a distally extending wall 2057 that mates with a vacuum base 2030.

Figure 20B:
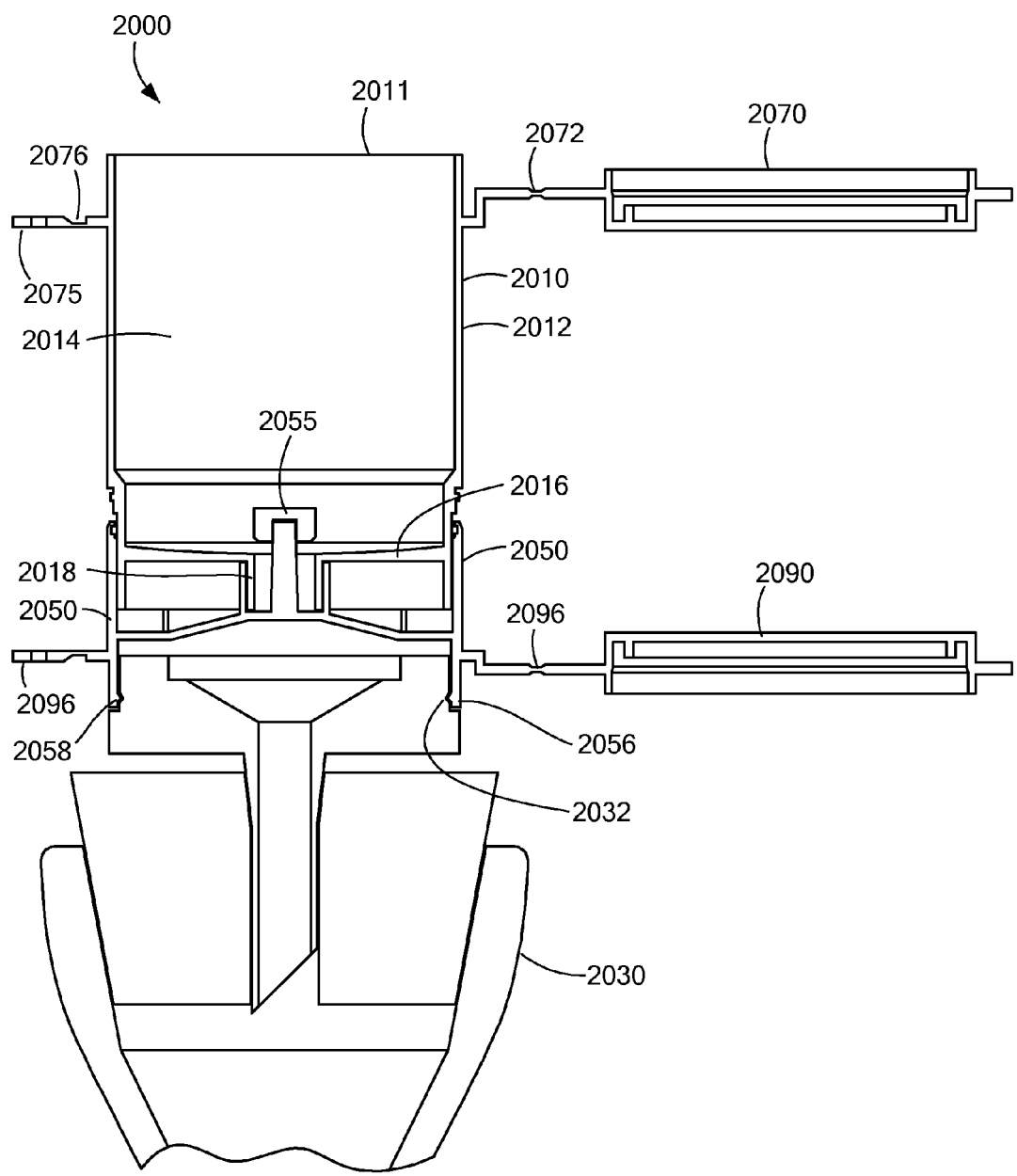
FIG. 20B schematically shows a cross-sectional view of the sample container of FIG. 20A in the open mode, in accordance with illustrative embodiments of the present invention.

The sample collection portion 2010 can mate with and be moveable relative to the valve case 2050. To that end, the sample collection portion 2010 can have a skirt 2020 that extends distally from the bottom wall 2016 of the sample collection portion 2010. Additionally, the valve case 2050 can have a wall 2052 that extends proximally towards the sample collection portion 2010 to form a recess 2054. As shown in FIGS. 20A and 20B, the skirt 2020 can extend into the recess 2054 formed by the wall 2052. In order to secure the sample collection portion 2010 to the valve case 2050 and provide for the relative movement between the two, various embodiments can have a series of protrusions and indents on the skirt 2020 and/or the wall 2052. For example, the skirt 2020 can have a series of protrusions that engage a series of indents on the wall 2052. Additionally or alternatively, the wall 2052 can have a series of protrusions that engage indents on the skirt 2020. As discussed in greater detail below, the protrusions can move in and out of the indents (e.g., between a number of "locked" positions) as the sample collection portion 2010 is moved relative to the valve case 2050 (e.g., in a telescoping manner).

Additionally or alternatively, as shown in FIG. 20A, the sample container 2000 can have locking mechanism that prevents the premature and/or accidental relative movement between the sample collection potion 2010 and the valve case 2050. For example, the sample container 2000 can have a peel tab 2060 and a peel strip 2065 that essentially holds the sample collection portion 2010 to the valve case 2050 and prevents the relative movement. To remove the peel tab 2060 and peel strip 2065 and allow the relative movement between the sample collection portion 2010 and the valve case 2050 (e.g., just prior to filtration), a user may pull the peel tab 2060 and remove the peel strip 2065 by peeling it off of the sample container 2010. Once the peel strip 2065 is removed, the sample collection container 2010 is free to move relative to the valve casing 2050 to open the plug valve 2055.

In a manner similar to the embodiments described above, the sample container 2000 can also have a top cap 2070 that covers the open end 2011 of the sample collection portion 2010 (when closed) and is connected to the sample collection portion 2010 with a hinge 2072 (e.g., a living hinge). To ensure that the sample and/or sample container 2000 has not been tampered with, the sample container can have a tamper evident latch 2075 attached to the sample collection portion 2010 via a hinge 2076. When the top cap 2070 is closed (e.g., after collecting the sample), the taper evident latch 2075 can be closed over a projection 2077 extending from the top cap 2070 such that the projection 2077 extends through a hole passing through the latch 2075, snapping/locking the latch 2075 into place. The projection 2077 can be shaped (e.g., arrow shaped, T-shaped, etc.) such that, once the latch 2075 snaps into place, it can not be removed unless it is broken. In this manner, if the latch 2075 is not broken, the user/lab technician can be confident that the sample has not been tampered with.

It is important to note that although the tamper evident latch 2075 is described above as being attached to the sample collection portion 2010 and closing over a projection 2077 on the top cap 2070, other configurations may be used. For example, the latch may be connected to the top cap 2070 via a hinge and may close over a projection extending from the sample collection portion 2010.

Like the sample collection portion 2010, the valve case 2050 can also have a cap (e.g., a bottom cap 2090) that covers the bottom of the valve case 2050. Additionally or alternatively, the valve case 2050 can include a removable seal 2098 that covers at least a portion the bottom 2056 of the valve case 2050 to help maintain the sterility of the sample container 2000. As discussed below, this seal 2098 should be removed prior to placing the sample container 2000 onto the vacuum (e.g., to allow the vacuum to be applied to the system).

Figure 21:
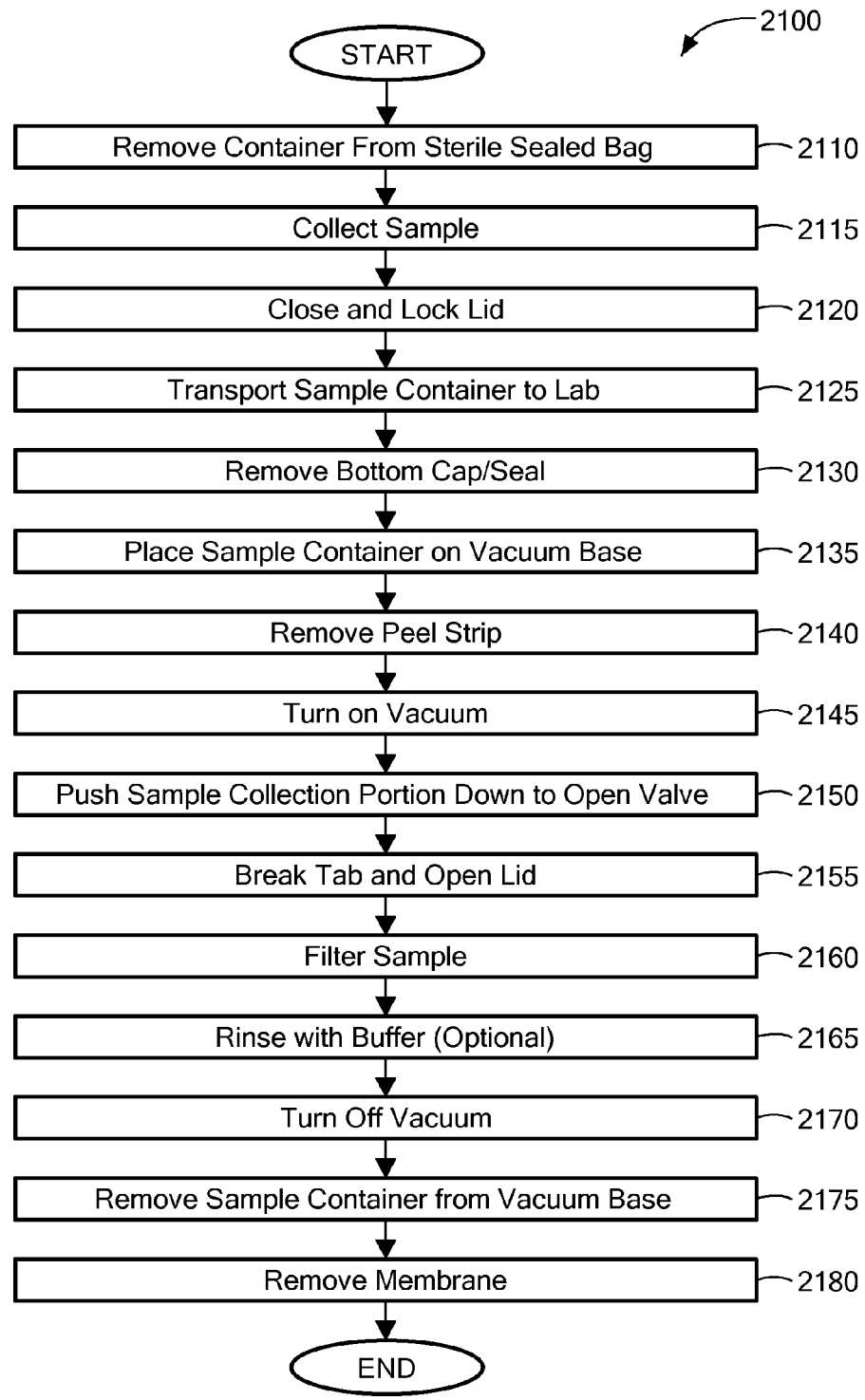
FIG. 21 shows a process of using the sample container shown in FIGS. 20A *and* 20B in accordance with illustrative embodiments of the present invention.
Figure 22A:
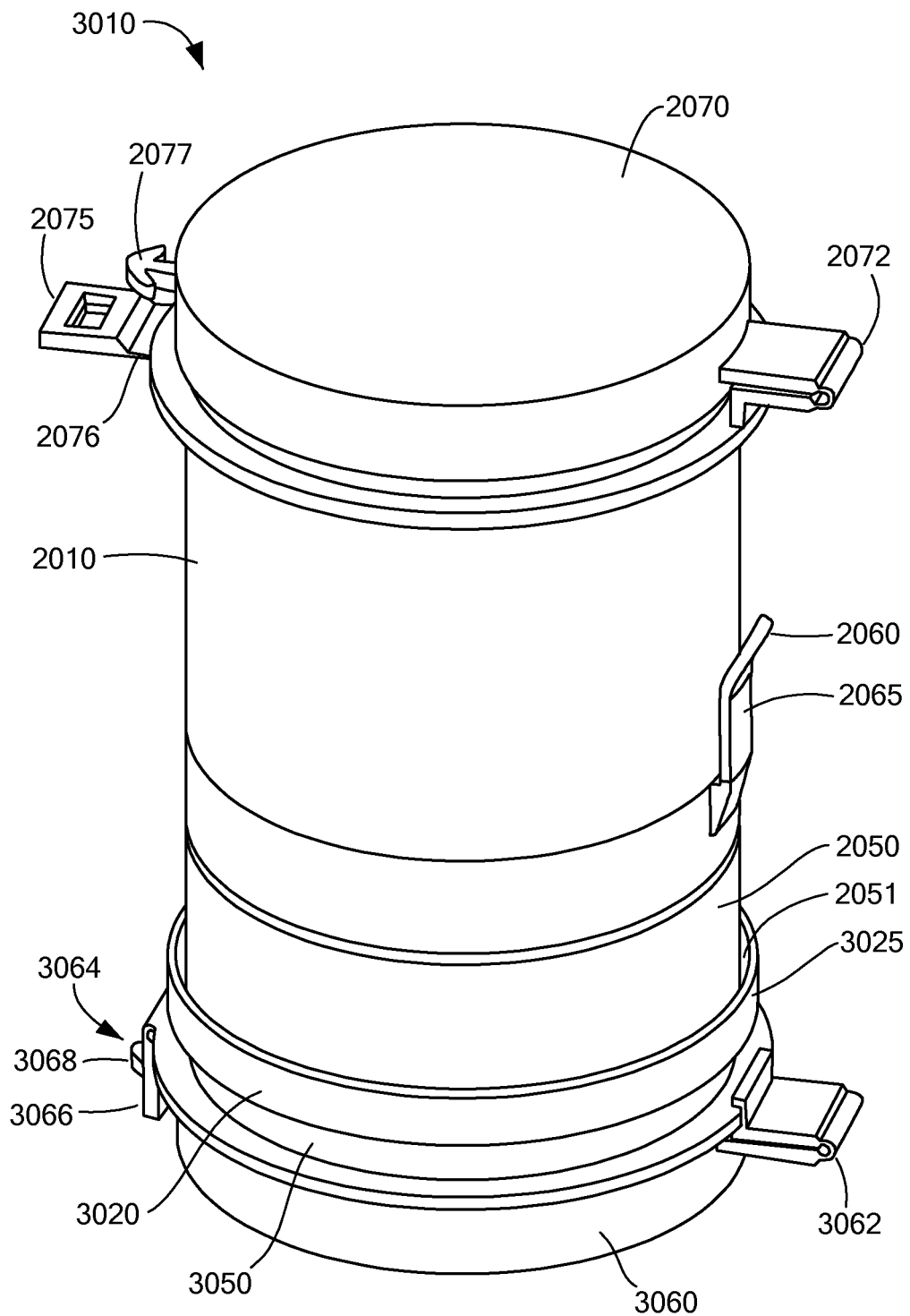
FIG. 22A schematically shows a perspective view of another embodiment of a sample container and filtration device in the closed mode, in accordance with illustrative embodiments of the present invention.
Figure 22B:
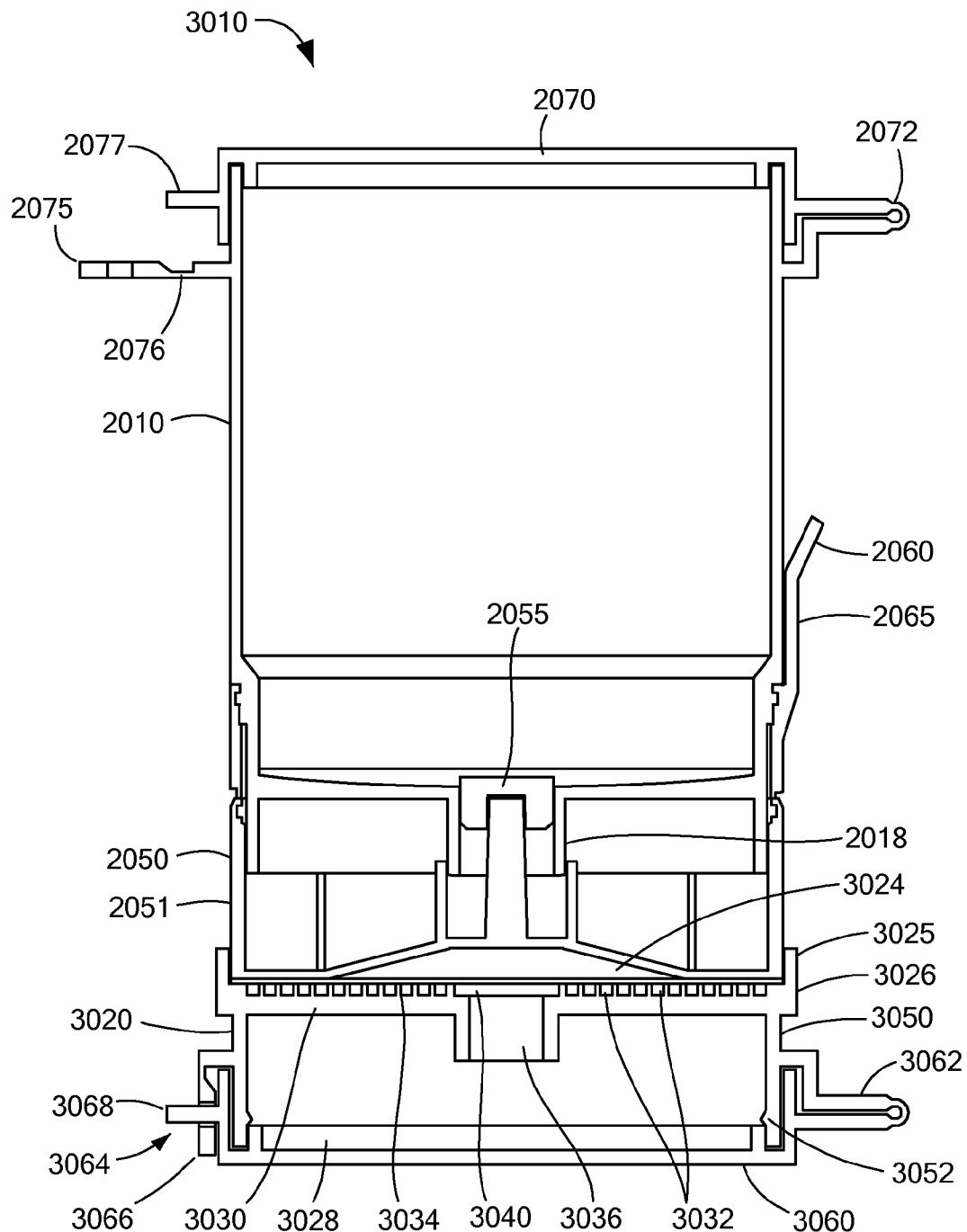
FIG. 22B schematically shows a cross-sectional view of the sample container and filtration device shown in FIG. 22A in the closed mode, in accordance with illustrative embodiments of the present invention.
Figure 22C:
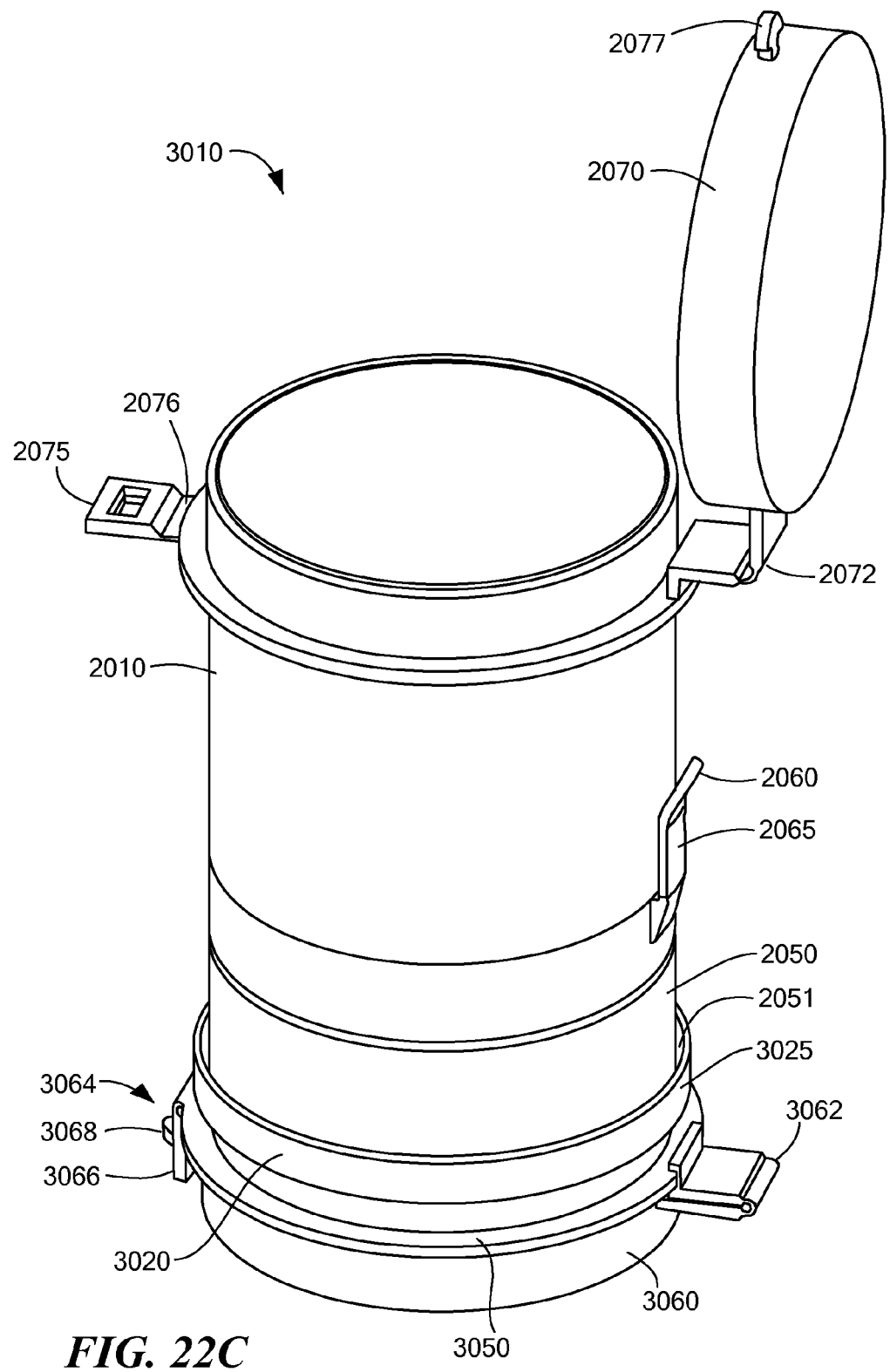
FIG. 22C schematically shows a perspective view of the device shown in FIG. 22A with the top lid open, in accordance with illustrative embodiments of the present invention.
Figure 22D:
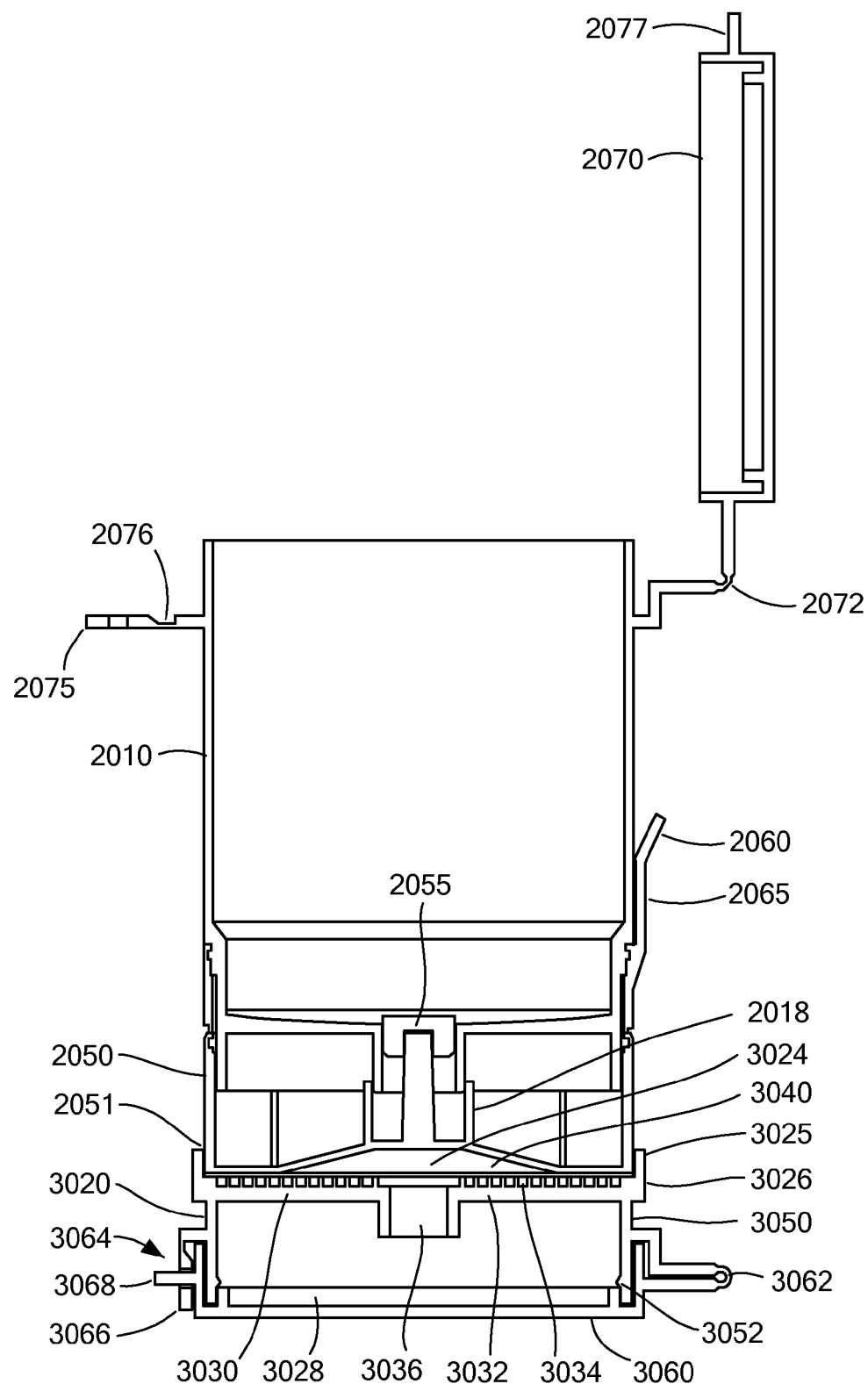
FIG. 22D schematically shows a cross-sectional view of the sample container and filtration device shown in FIG. 22A with the top lid open, in accordance with illustrative embodiments of the present invention.
Figure 22E:
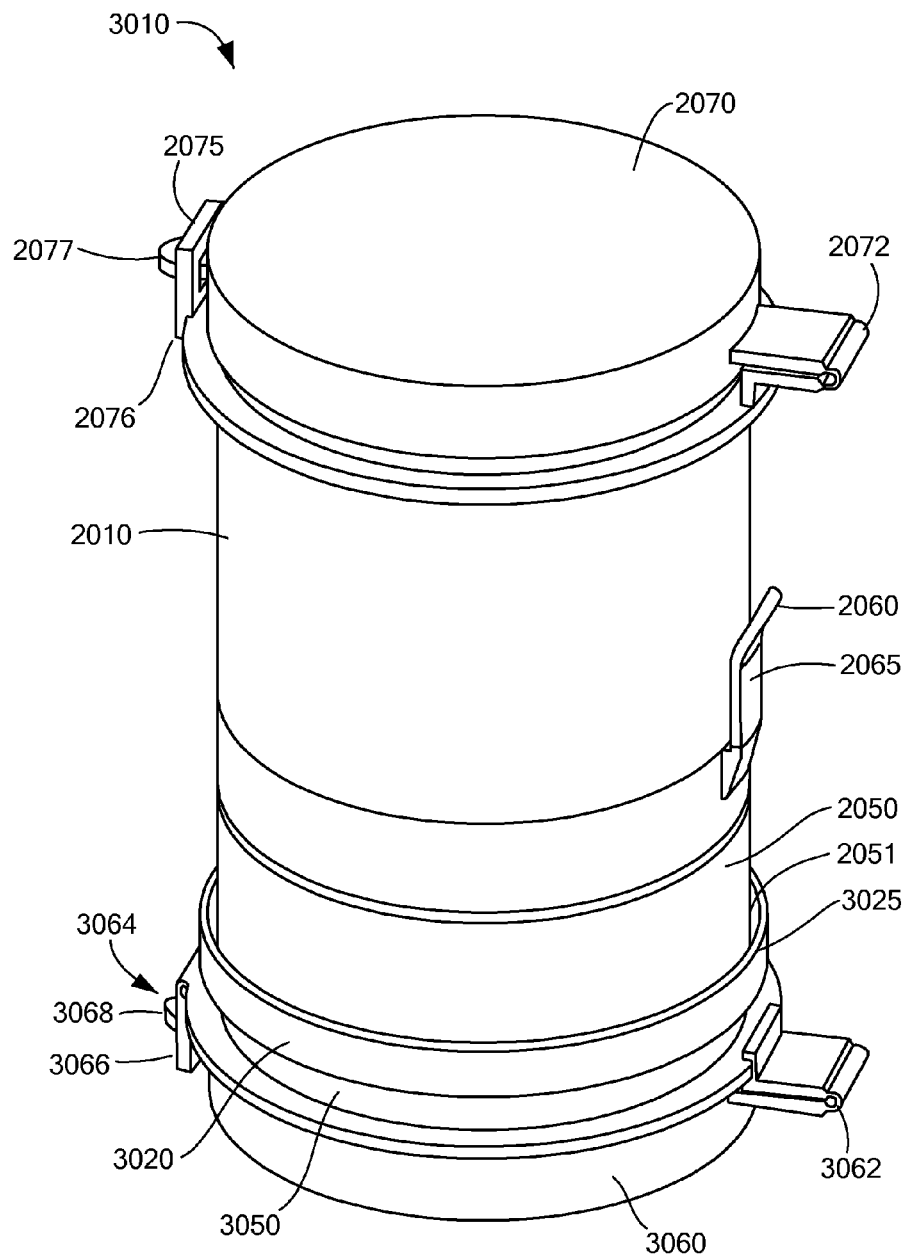
FIG. 22E schematically shows a perspective view of the device shown in FIG. 22A with the tamper evident latch closed, in accordance with illustrative embodiments of the present invention.
Figure 22F:
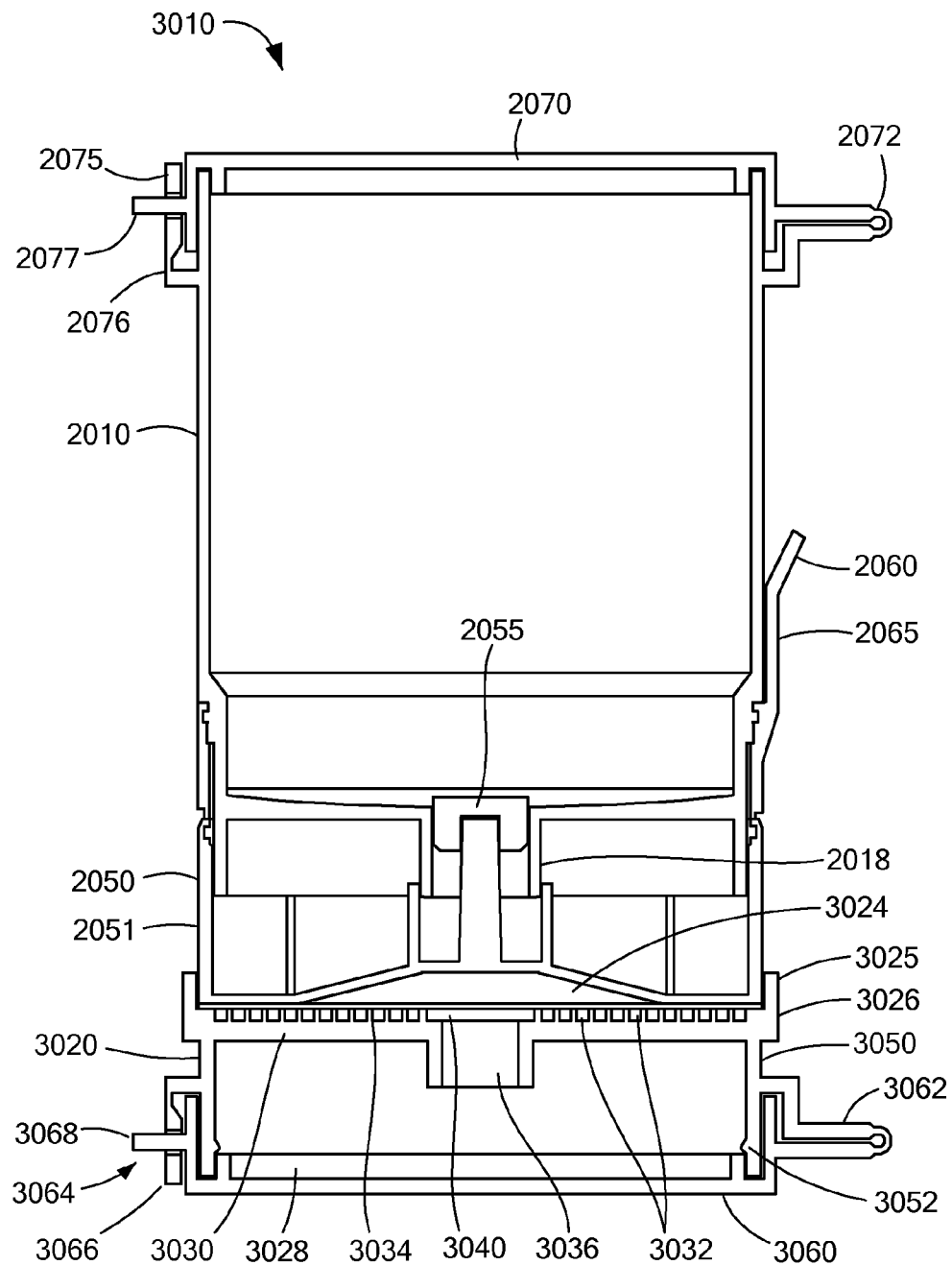
FIG. 22F schematically shows a cross-sectional view of the sample container and filtration device shown in FIG. 22A with the tamper evident latch closed, in accordance with illustrative embodiments of the present invention.
Figure 22G:
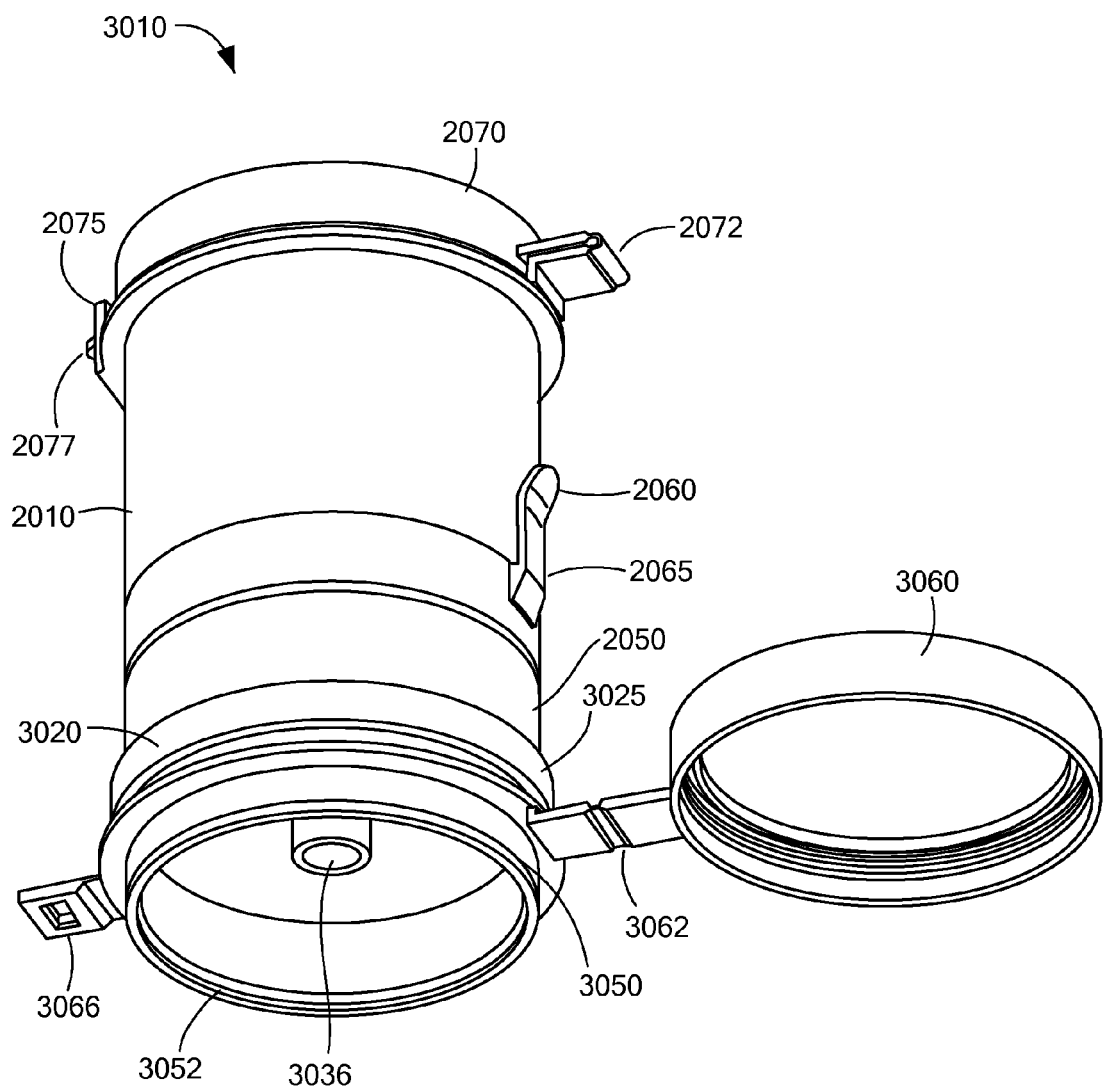
FIG. 22G schematically shows a perspective view of the device shown in FIG. 22A with the bottom lid open, in accordance with illustrative embodiments of the present invention.
Figure 22H:
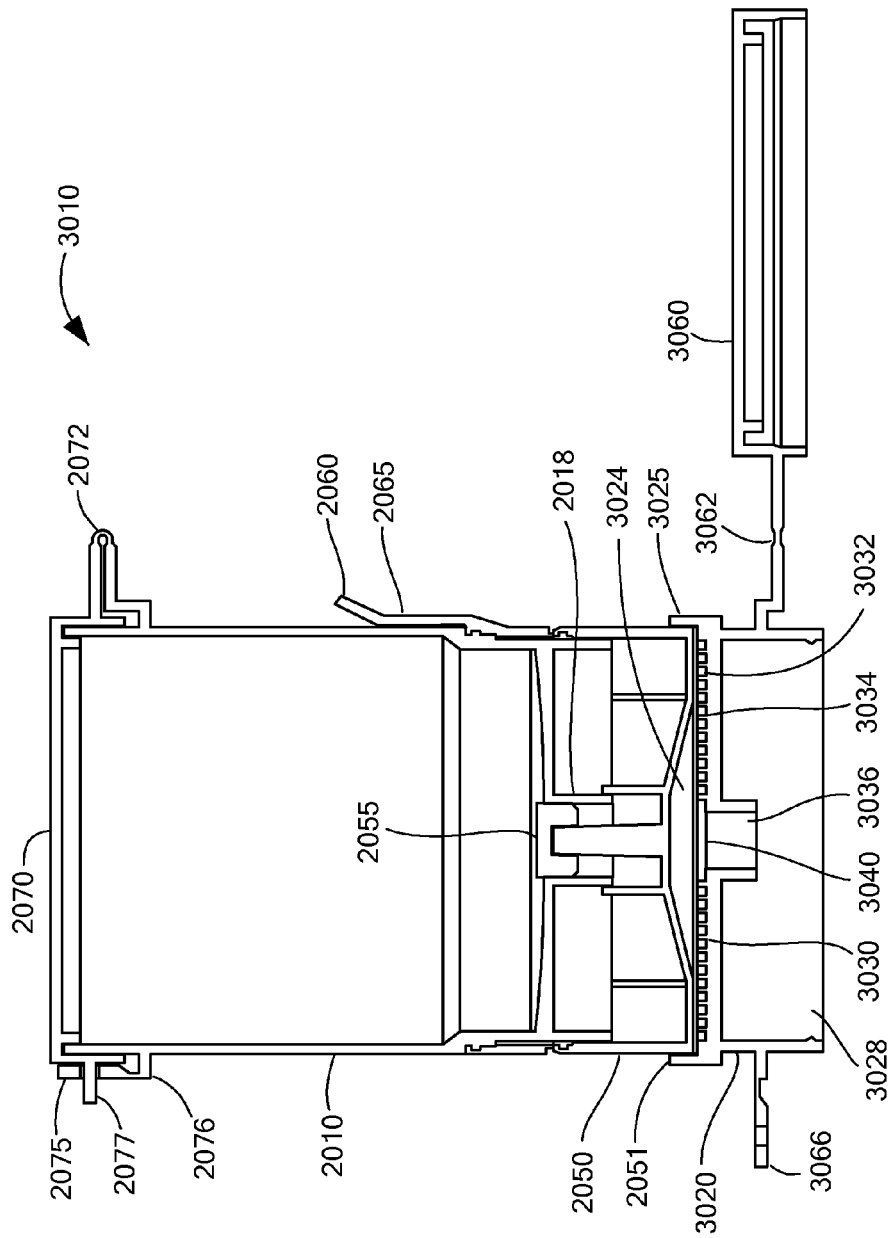
FIG. 22H schematically shows a cross-sectional view of the sample container and filtration device shown in FIG. 22A with the bottom lid open, in accordance with illustrative embodiments of the present invention.

FIG. 21 shows a process 2100 illustrating one use of the sample container 2000 shown in FIGS. 20A and 20B. After removing the sample container 2000 from any packaging (e.g., a sterile sealed bag) (Step 2110) and opening the top cap 2070, the user may then collect the sample within the sample collection portion 2010 (e.g., within the interior cavity 2014) (Step 2115), close and lock the top cap 2070 using the tamper evident latch (Step 2120), and transport the sample to the laboratory (Step 2125).

Once in the laboratory and the user/lab technician is ready to filter the sample, the user/technician can open the bottom cap 2090 and/or remove the seal 2098 from the bottom of the valve case 2050 (Step 2130), and place the sample container 2000 onto the vacuum base 2030 (Step 2135). As mentioned above, in some embodiments, the valve case 2050 can have a distally extending wall 2057 that mates with the vacuum base 2030. In such embodiments, the wall 2057 can be placed over vacuum base 2030 and a protrusion 2058 on the wall 2057 can engage an indent 2032 on the vacuum base 2030 (FIG. 20B) to lock the sample container 2000 to the vacuum base 2030.

After locking the sample container 2000 to the base 2030, the user/technician can then remove the peel strip 2065 by pulling the peel tab 2060 and peeling off the peel strip 2065 (Step 2140). The user/technician may then turn on the vacuum (Step 2145), and push the sample collection 2010 down to open the plug valve 2055 (e.g., move it from the position shown in FIG. 20A to the position shown in FIG. 20B) and allow fluid flow through the outlet (Step 2150). For example, as the sample collection portion 2010 is pushed down (e.g., as it moves relative to the valve case 2050 in a telescoping manner), the valve plug 2055 will move (relative to the sample collection portion 2010) from the position shown FIG. 20A in which it blocks/closes the outlet 2018 to the position shown in FIG. 20B in which the valve plug 2055 no longer blocks/closes the outlet 2018.

It is important to note that, although the valve operation described above causes the valve plug 2055 to move into the interior 2014 of the sample collection portion 2010 (e.g., because the sample collection portion 2010 is pushed downward), other embodiments can utilize different valve actuation. For example, the user/technician can move the sample collection portion 2010 upwards, causing the plug valve 2055 to move downward relative to the outlet 2018 of the sample collection portion 2010 to open the outlet 2018.

After opening the valve (e.g., such that the valve plug 2055 no longer block/closes the outlet 2018), the user/technician can break the tamper evident latch 2075 and open the top cap 2070 (Step 2155). Once the top cap 2070 is opened and the vacuum is on, the vacuum applied to the sample container 2000 will cause the sample to be drawn from the interior cavity 2014, out the outlet 2018 of the sample collection portion 2010, and through a filter membrane located on the vacuum base 2030 to filter the sample (Step 2160). After filtration is complete, the user/technicians may optionally rinse the sample container 2000 (e.g., the interior cavity 2014) with a buffer solution (Step 2165) and turn off the vacuum (Step 2170). The user/technician may then remove the sample container 2000 from the vacuum base 2030 by disconnecting the valve casing 2050 from the base 2030 (Step 2175), and remove the filter membrane from the vacuum base (Step 2180) for further processing.

Although the embodiments discussed above utilize a filter membrane that is not part of the sample container 2000, other embodiments may have a filter membrane that is contained within the sample container (e.g., the filter membrane is part of the sample container and filtering apparatus). For example, as shown in FIGS. 22A-22H, in addition to the sample collection portion 2010 and the valve case 2050, some embodiments of the sample container and filtration apparatus 3010 may also have a coupling portion 3020 (e.g., a vacuum base coupling portion) located distal to the valve case 2050. The coupling portion 3020 may be secured to the valve case 2050 in similar manner to how the valve case 2050 is secured to the sample collection portion 2010, however, the ability to move the coupling portion 3020 relative to the valve case 2050 is not necessary. For example, the coupling portion 3020 can have an annular wall 3025 that extends proximally and defines a recess 3024. The valve case 2050 (e.g., the valve case distal wall 2057) may then sit within the recess 3024. In order to lock the valve case 2050 in place, the valve case 2050 can have a protrusion extending from the exterior wall 2051 of the valve case 2050. This protrusion can, in turn, snap into an indentation within the inner surface 3026 of the annular wall 3025. Additionally or alternatively, the inner surface 3026 of the annular wall 3025 can have a protrusion that snaps into an indentation within the exterior wall 2051 of the valve case 2050.

The coupling portion 3020 may also include a filter support surface 3030 that supports the filter membrane 3040 used to filter the collected sample. In order to improve the flow of fluid through the filter membrane 3040, in some embodiments, the filter support surface 3030 may include support ribs 3032 and channels 3034. In such embodiments, the filter membrane 3040 can sit on the support ribs 3032, and the channels 3034 can channel/direct the fluid passing though the filter membrane 3040 towards a fluid path 3036 (e.g., an outlet) through the filter support surface 3030. In some embodiments, the valve case 2050 can have an annular surface 2053 that contacts and seals against the filter membrane 3040 to prevent leakage past the filter membrane 3040.

In order to facilitate the connection/coupling of the sample container and filtration apparatus 3010 with the vacuum base 2030, the coupling portion 3020 can include a coupling skirt 3050 that extends distally from the filter supports surface 3030. As discussed in greater detail below, the coupling skirt 3050 can mate with the vacuum base 2030 and can include an annular protrusion 352 that extends/snaps into an indentation 2032 on the vacuum base 2030 to secure the coupling portion 3020 (and, therefore, the sample container and filtration apparatus 3010) to the vacuum base 2030.

Like the sample collection portion 2010, the coupling portion 3020 can also have a cap (e.g., bottom cap 3060) that covers the bottom opening 3028 of the coupling portion 3020 to help preserve the sterility of the filter membrane 3040. Like the top cap 2070 described above, the bottom cap 3060 can also be connected to the sampling device 3010 (e.g., the coupling portion 3020) via a hinge 3062 and can have a tamper evident latching mechanism 3064 with a latch 3066 and a tab 3068.

Figure 23A:
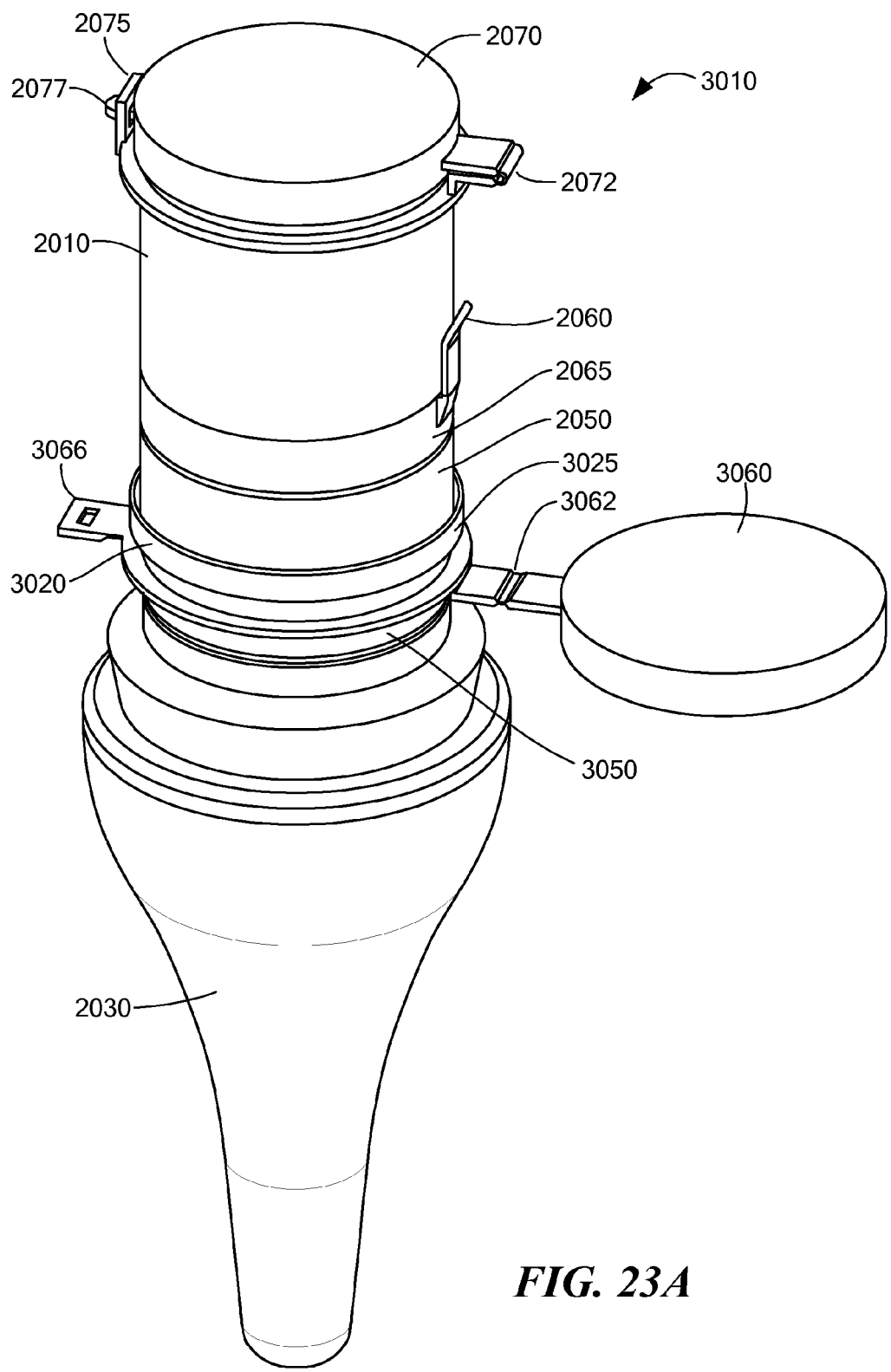
FIG. 23A schematically shows a perspective view of the device shown in FIG. 22A mounted on a vacuum base, in accordance with illustrative embodiments of the present invention.
Figure 23B:
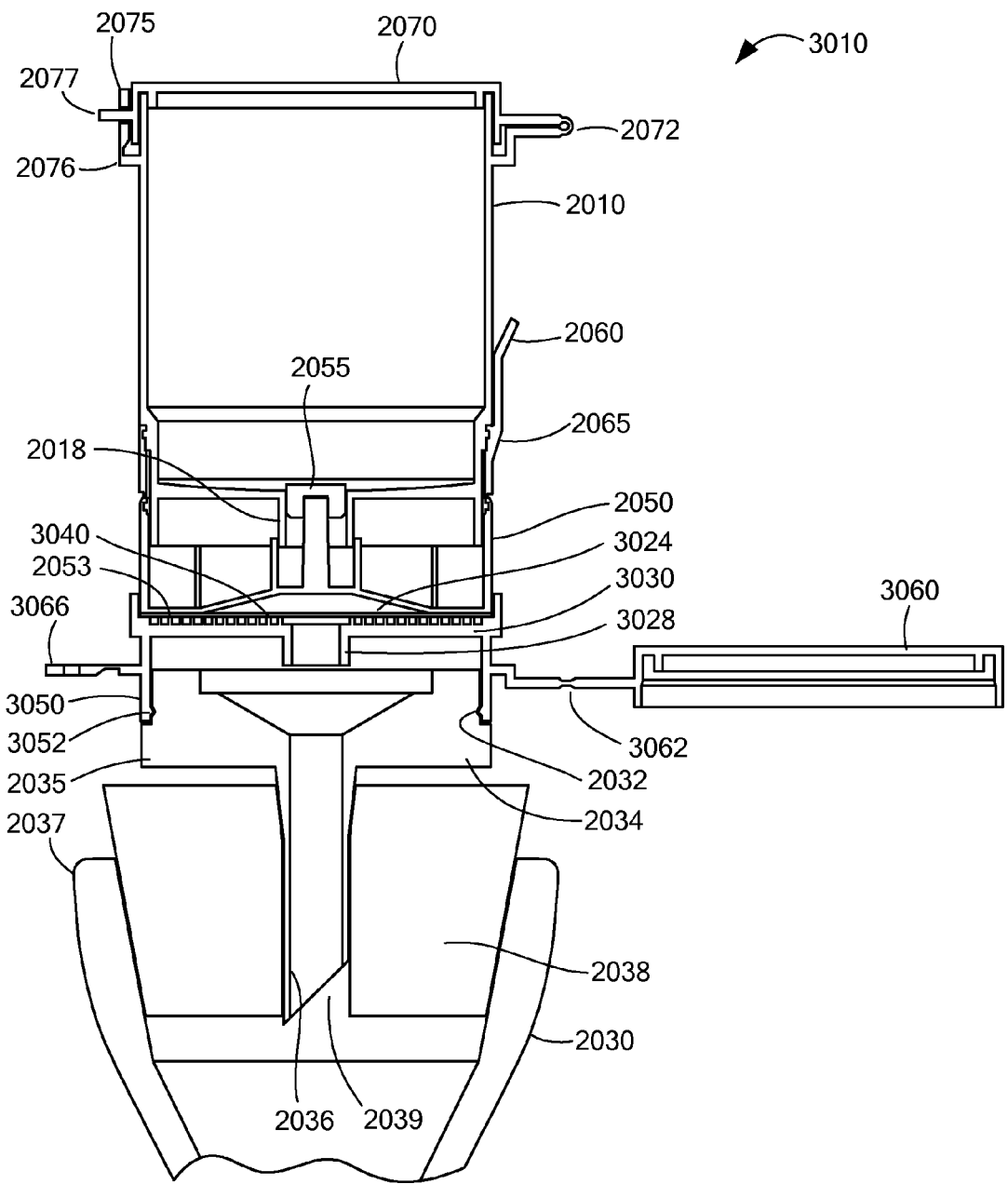
FIG. 23B schematically shows a cross-sectional view of the sample container and filtration device shown in FIG. 22A mounted on the vacuum base, in accordance with illustrative embodiments of the present invention.
Figure 23C:
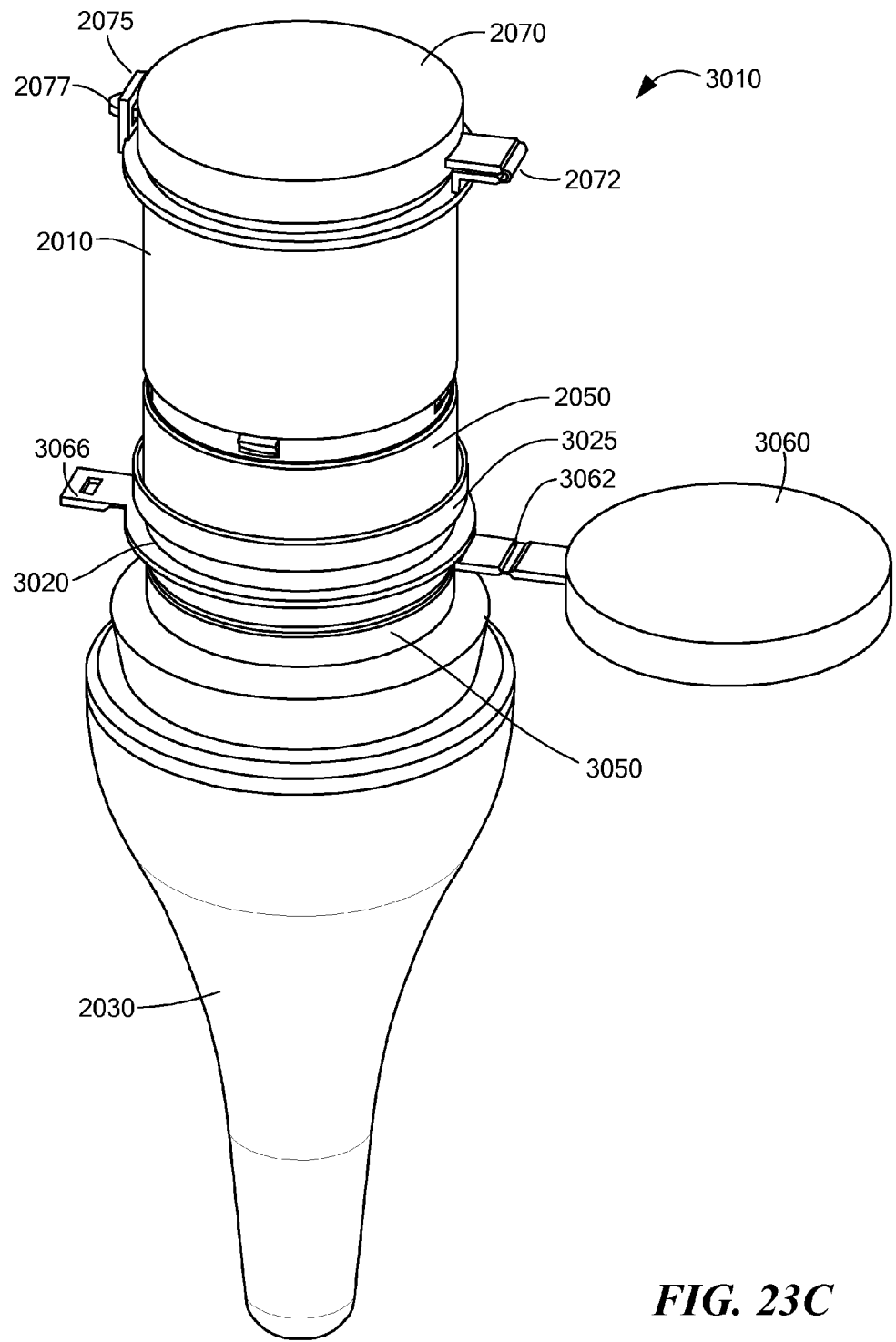
FIG. 23C schematically shows a perspective view of the device shown in FIG. 22A mounted on a vacuum base and in an open mode, in accordance with illustrative embodiments of the present invention.
Figure 23D:
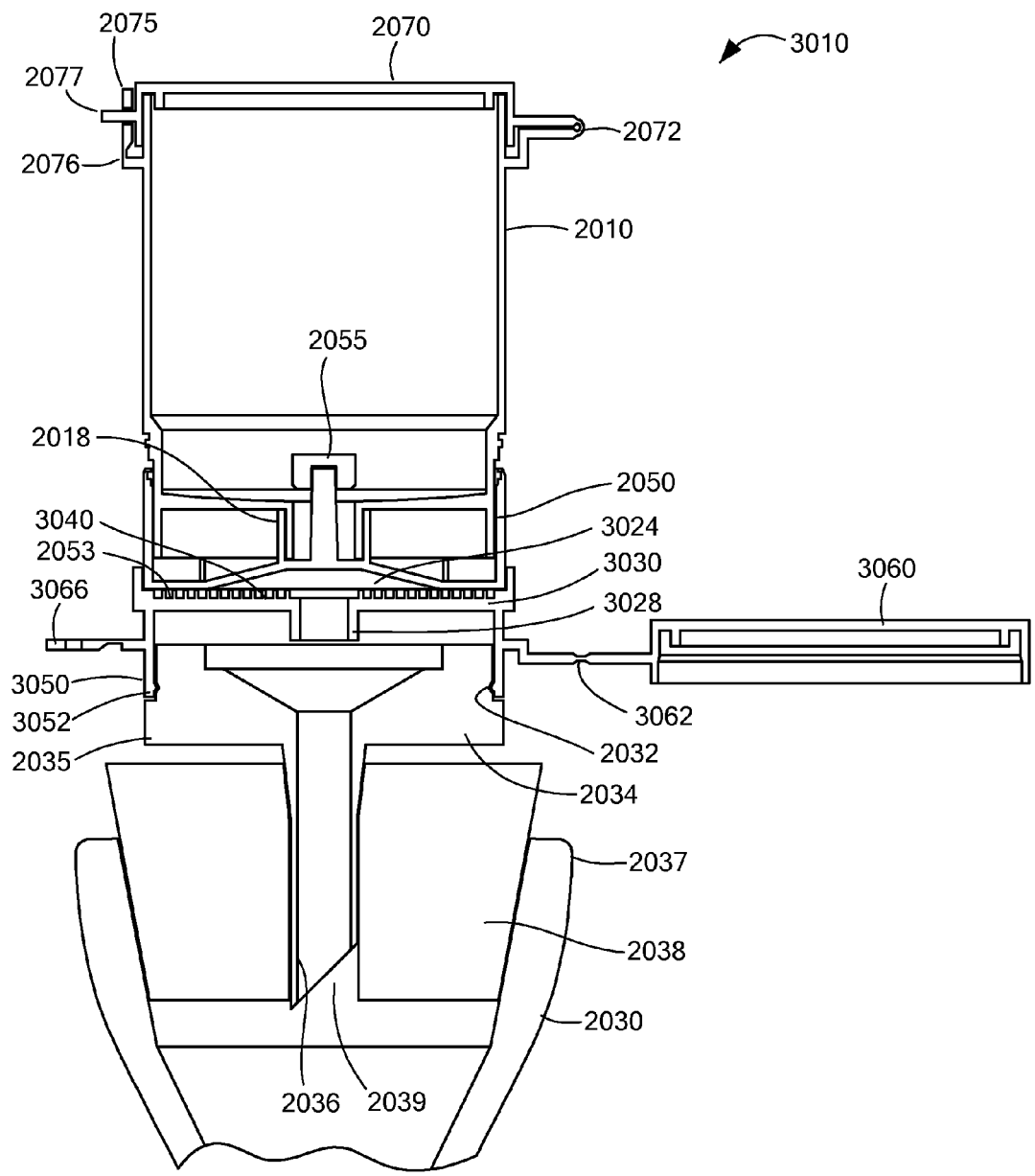
FIG. 23D schematically shows a cross-sectional view of the sample container and filtration device shown in FIG. 22A mounted on the vacuum base and in an open mode, in accordance with illustrative embodiments of the present invention.
Figure 23E:
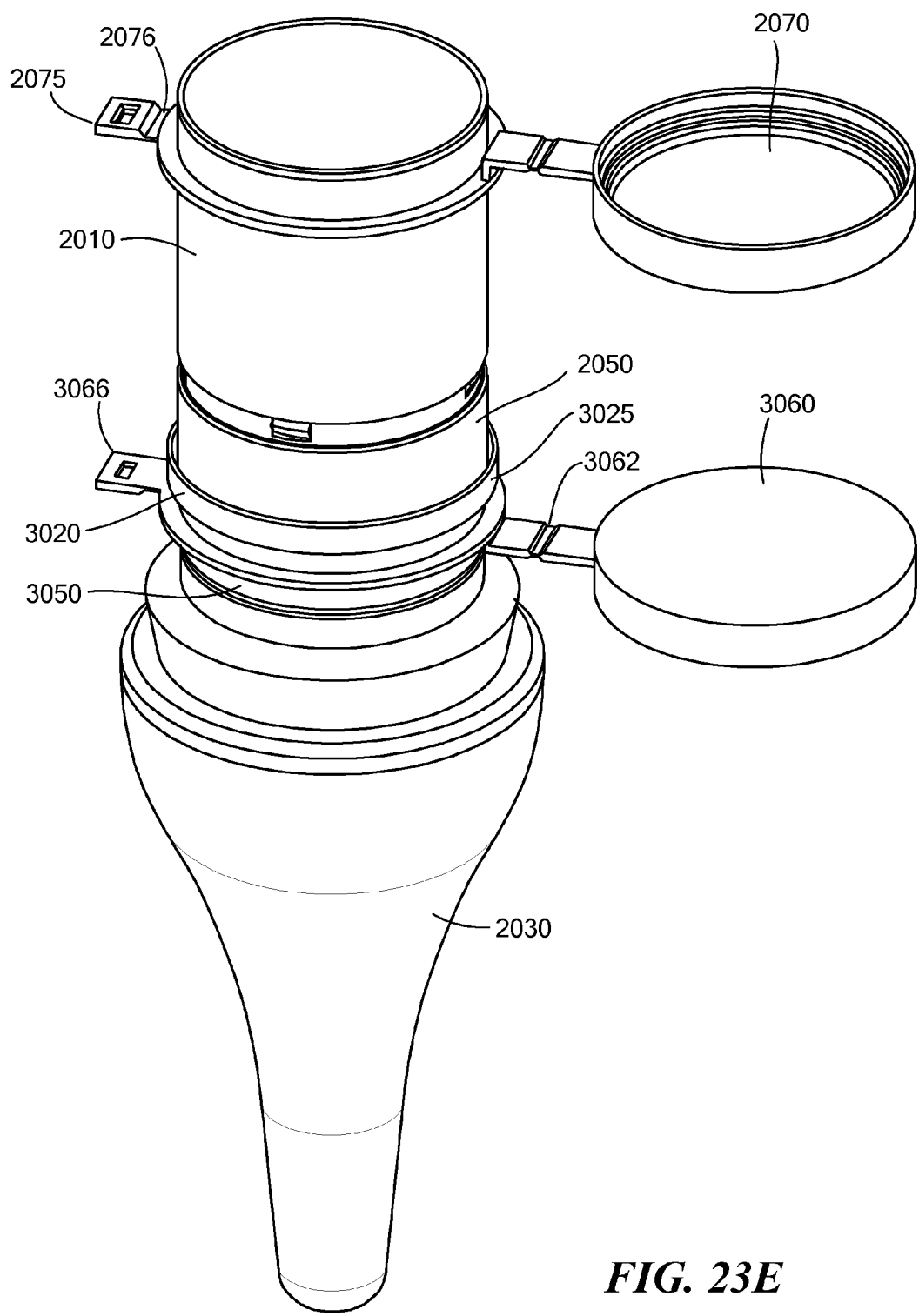
FIG. 23E schematically shows a perspective view of the device shown in FIG. 22A mounted on a vacuum base with the top cap open, in accordance with illustrative embodiments of the present invention.
Figure 23F:
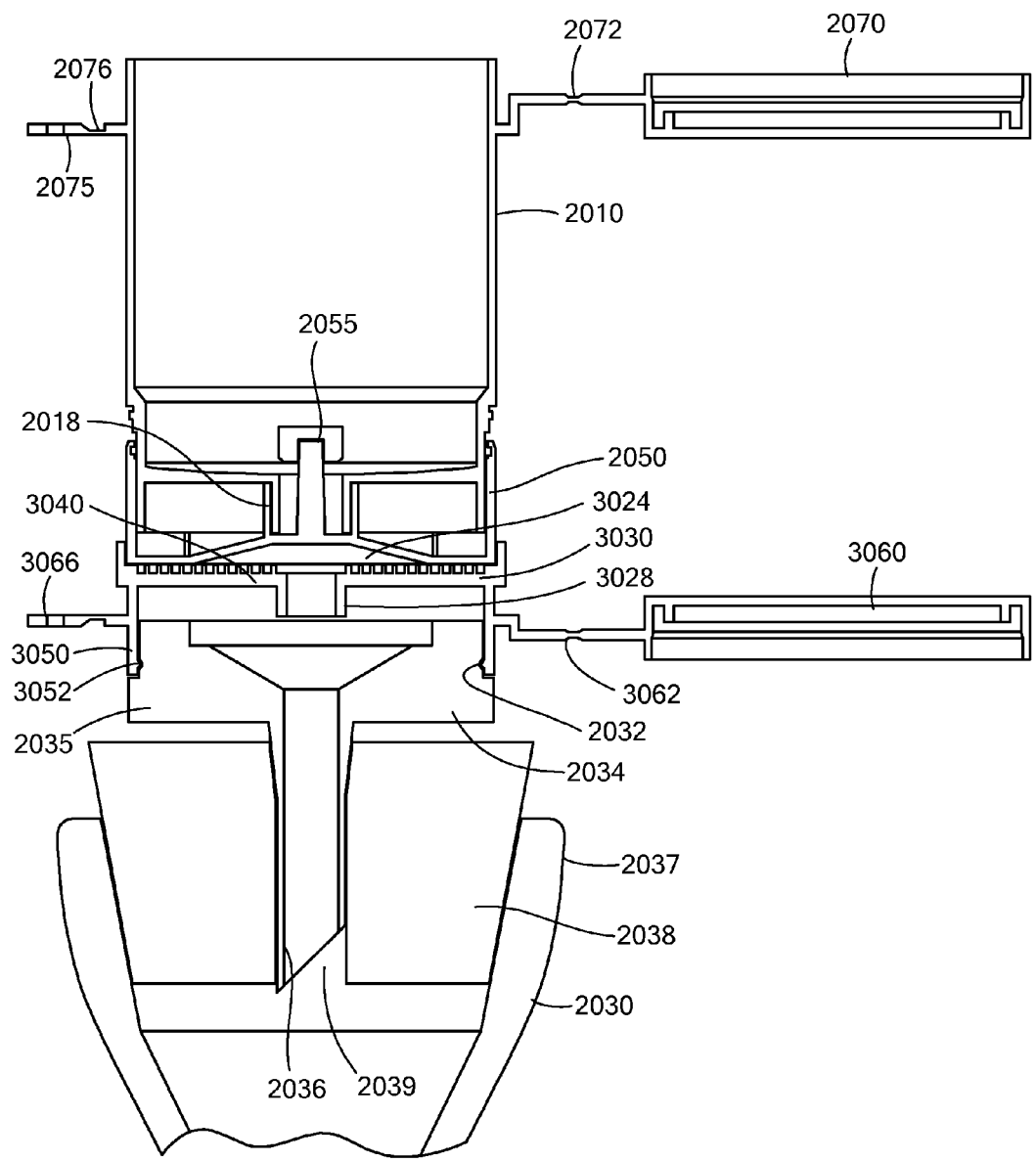
FIG. 23F schematically shows a cross-sectional view of the sample container and filtration device shown in FIG. 22A mounted on the vacuum base with the top cap open, in accordance with illustrative embodiments of the present invention.
Figure 23G:
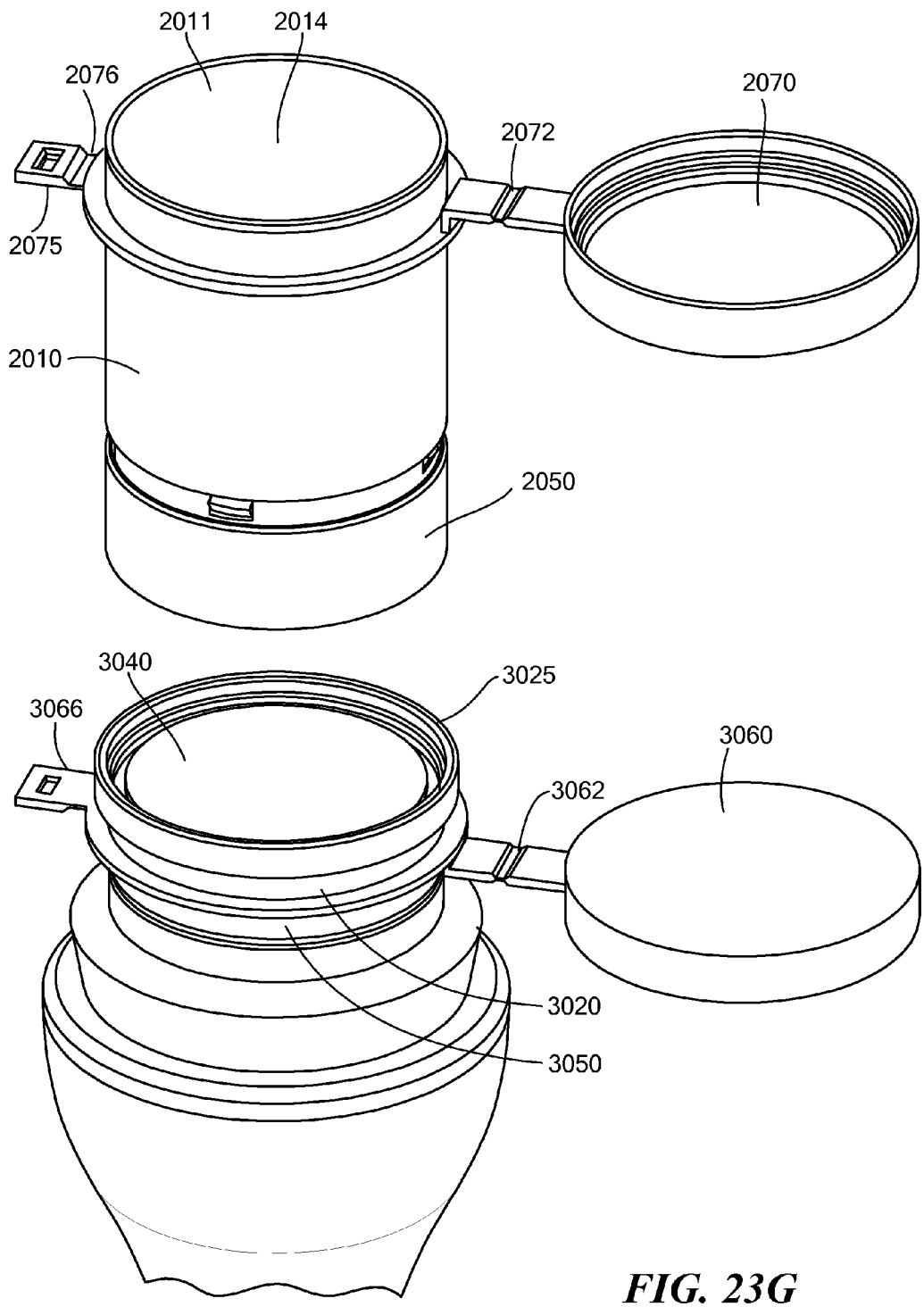
FIG. 23G schematically shows a perspective view of the device shown in FIG. 22A with a portion of the device disengaged, in accordance with illustrative embodiments of the present invention.
Figure 23H:
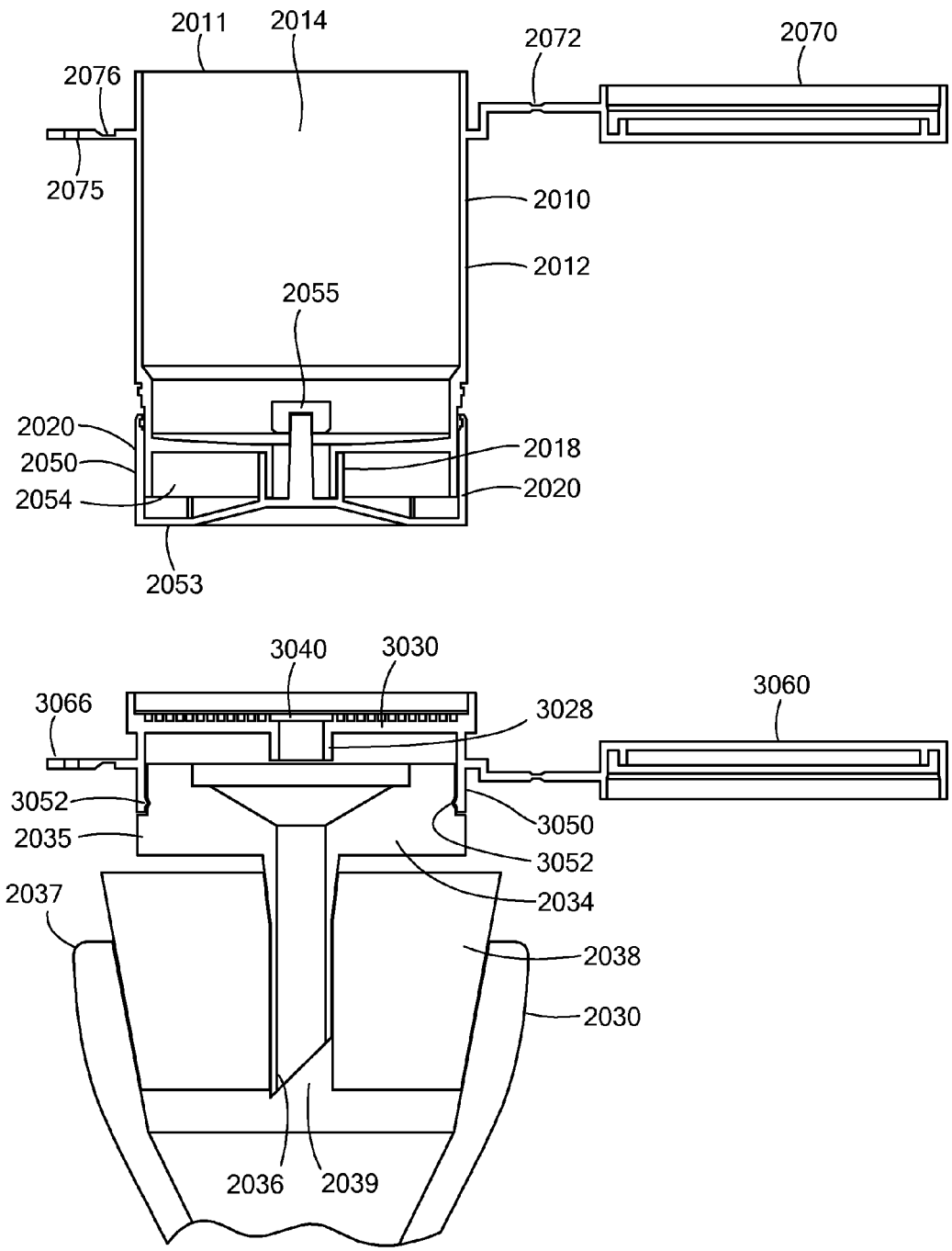
FIG. 23H schematically shows a cross-sectional view of the sample container and filtration device shown in FIG. 22A with a portion of the device disengaged, in accordance with illustrative embodiments of the present invention.
Figure 23I:
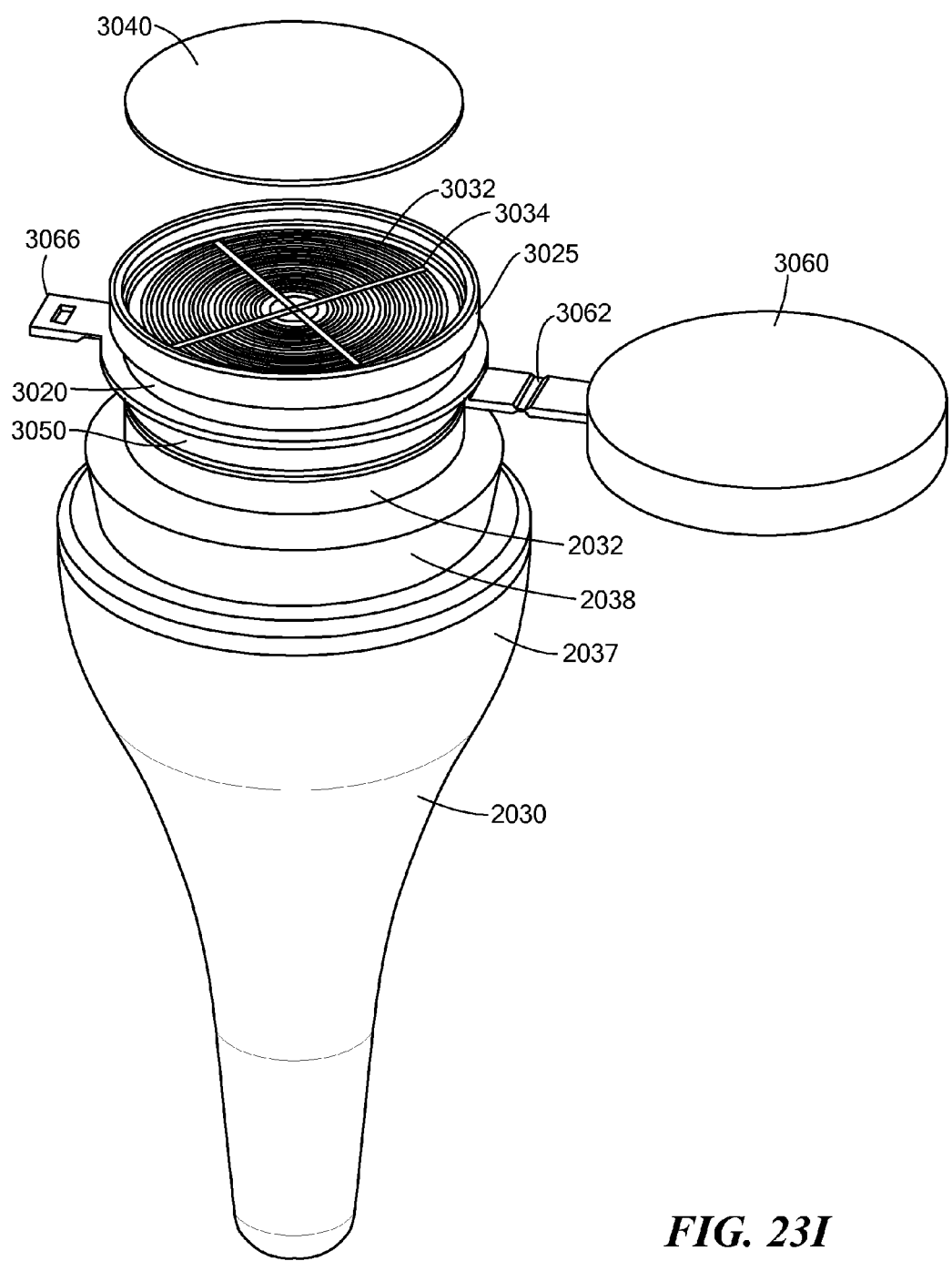
FIG. 23I schematically shows a perspective view of the device shown in FIG. 22A with a portion of the device disengaged and the filter exposed, in accordance with illustrative embodiments of the present invention.
Figure 23J:
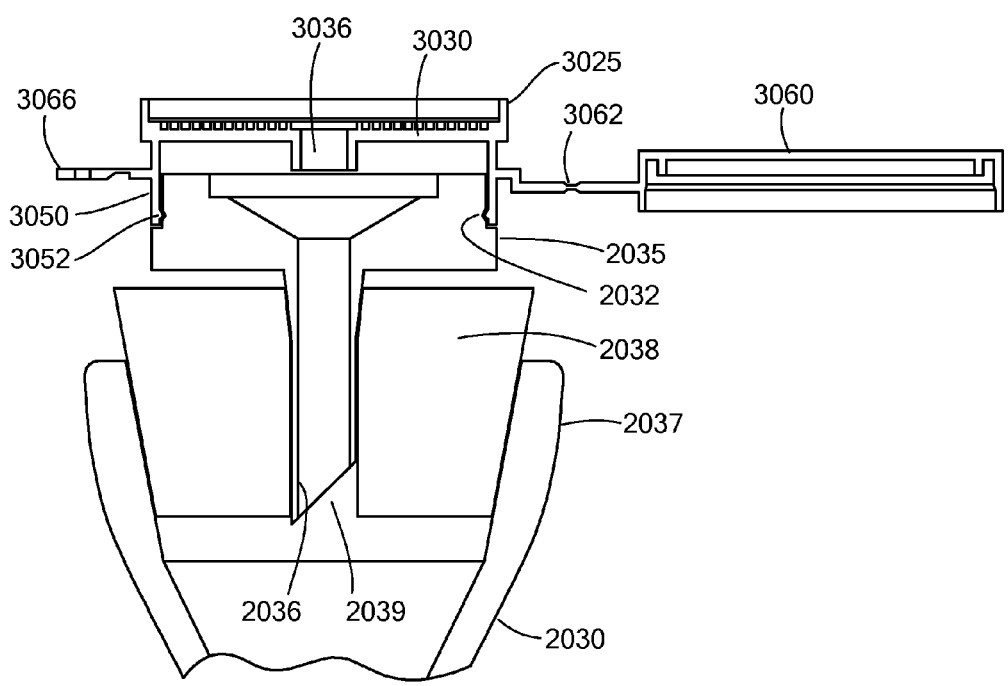
FIG. 23J schematically shows a cross-sectional view of the sample container and filtration device shown in FIG. 22A with a portion of the device disengaged and filter exposed, in accordance with illustrative embodiments of the present invention.
Figure 24:
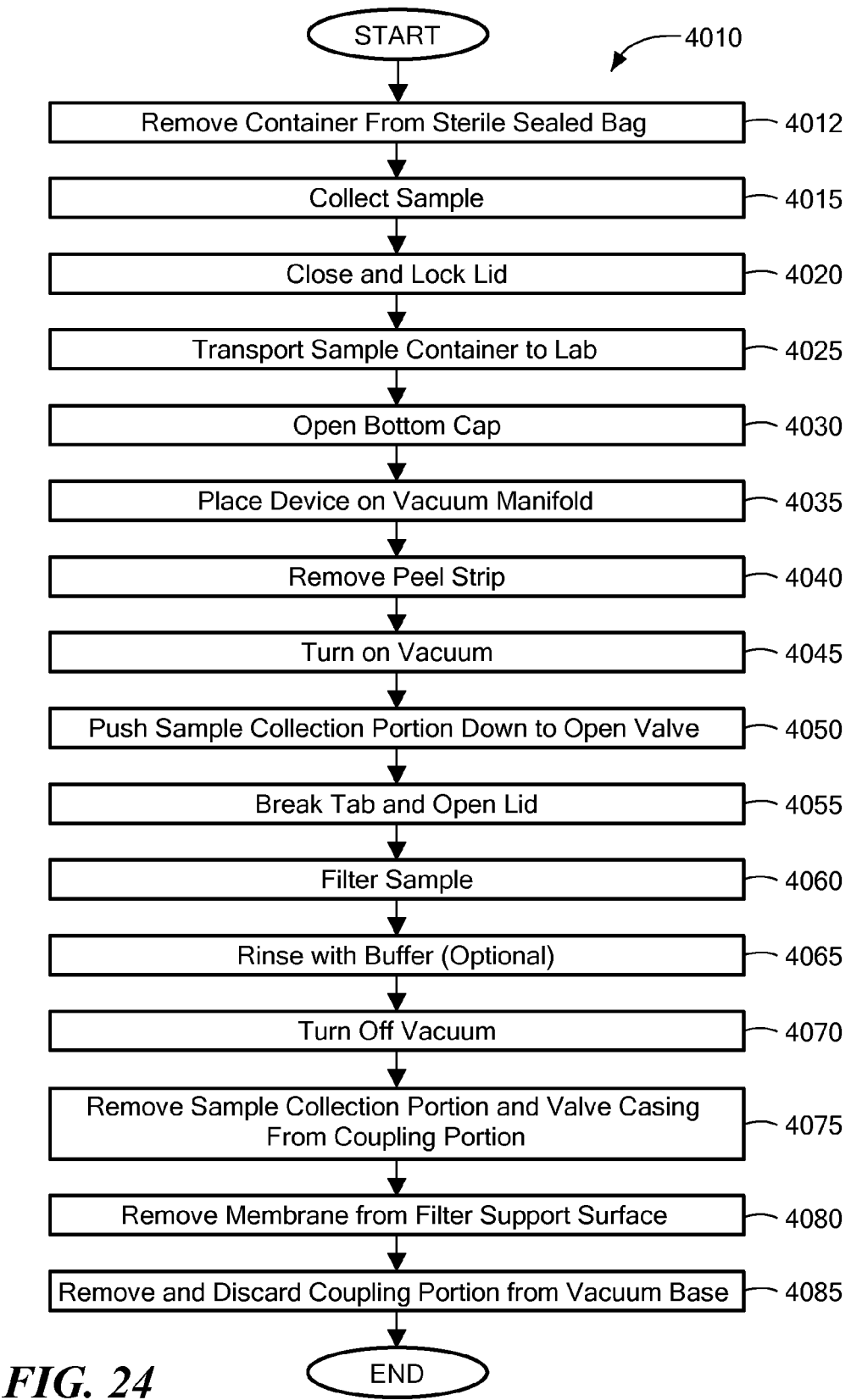
FIG. 24 shows a process of using the sample container shown in FIG. 22A in accordance with illustrative embodiments of the present invention.

FIGS. 23A-23J show the sample container and filtration apparatus 3010 discussed above during the various steps of use, and will be discussed in conjunction with FIG. 24 which shows a process 4010 illustrating one use of the sample container and filtration apparatus 3010 shown in FIGS. 22A-22H. After removing the sample container and filtration apparatus 3010 from any packaging (e.g., a sterile sealed bag) (Step 4012) and opening the top cap 2070, the user may then collect the sample within the sample collection portion 2010 (e.g., within the interior cavity 2014) (Step 4015), close and lock the top cap 2070 using the tamper evident latch (Step 4020), and transport the sample to the laboratory (Step 4025).

Once the collected sample and the sample container and filtration apparatus 3010 are received in the laboratory and the technician is ready to filter the sample, the technician may confirm that the tamper proof latch 3064 is still in tact (e.g., to confirm that the sample has not been tampered with), break the latch 3064, and open the bottom cap 3060 (Step 4030). Once the bottom cap 3060 is open, the technician may place the device on the vacuum base 2030 (Step 4035; FIGS. 23A and 23B). As mentioned above, the coupling skirt 3050 can have an annular protrusion 352 that extends/snaps into an indentation 2032 within the vacuum base 2030. Therefore, once the annular protrusion 352 snaps into place, the sample container and filtration apparatus 3010 is secured to the vacuum base 2030.

In order to allow relative movement between the sample collection portion 2010 and the valve casing 2050 (e.g., to allow the valve to be opened), the technician may then remove the peel strip 2065 by pulling on the peel tab 2060 and peeling the strip 2065 off of the device 3010 (Step 4040; FIGS. 23C and 23D). To begin the filtration process and allow the sample to flow out of the sample collection portion 2010, the technician may then turn on the vacuum (Step 4045), and push the sample collection portion 2010 down which, in turn, causes the plug valve 2055 to move into the interior cavity 2014 and open the fluid path 2018 through the bottom wall 2016 of the sample collection portion 2010 (Step 4050; FIGS. 23C and 23D). Additionally, in order to improve fluid flow, the technician can also break the tamper evident latch 2075 on the top cap 2070, and open the top cap 2070 (Step 4055; FIGS. 23E and 23F). Once the fluid path 2018 and top cap 2070 are open, the vacuum applied by the vacuum base 2030 will draw the sample from sample collection portion 2010, through the fluid path 2018, through the filter membrane 3040, and out of the device 3010 (e.g., into the vacuum base 2030). As the sample passes through the filter membrane 3040, it is filtered (Step 4060) and any particulates within the sample are deposited on the filter membrane 3040.

After the filtration is complete and any optional rinsing is performed (Step 4065), the technician may turn off the vacuum (Step 4070), and remove the sample collection portion 2010 and valve casing 2050 from the coupling portion 3020 (Step 4075; FIGS. 23G and 23H). As mentioned above, the various components may be secured together using a snap fit type arrangement (e.g., the components can have protrusions and indents that cause the components to snap into place). Therefore, it is important to note that care must be taken when disconnecting the sample collection portion 2010 and valve casing 2050 from the coupling portion 3020 to ensure that the coupling portion 3020 is not inadvertently removed from the vacuum base 2030 (e.g., so that the filter membrane 3040 is exposed). To that end, in some embodiments, the snap fit connection between the coupling portion 3020 and the vacuum base 2030 can be stronger (e.g., it may take more force to disconnect) than the connection between of the valve casing 250 and the coupling portion 3020 and/or between the sample collection portion 2010 and the valve casing 2050.

Once the sample collection portion 2010 and the valve casing 2050 are disconnected from the coupling portion 3020, the filter membrane 3040 and the filter support surface 3030 are exposed, and the technician can remove the filter membrane 3040 from the support surface 3030, for example, using forceps (Step 4080; FIGS. 23I and 23J). The filter membrane 3040 can then be placed in a petri dish and further processed, as necessary. Additionally, the technician may also remove the coupling portion 3020 from the vacuum base 2030 and discard the coupling portion 3020 (e.g., along with the sample collection portion 2010 and the valve casing 2050) (Step 4085).

FIGS. 25A-25E show an additional embodiment of a sample collection and filtration device 5010 that has some features similar to the device shown in FIGS. 22A-H. For example, like the embodiment shown in FIGS. 22A-22H, the sample collection and filtration device 5010 shown in FIGS. 25A-25E has a sample collection portion 5020 with a wall 5022 defining an interior volume 5024 (e.g., for collecting the sample), and a top cover 5030 with a tamper evident latch 5040. However, unlike the embodiment shown in FIGS. 22A-22H, the device 5010 shown in FIGS. 25A-25E does not have a separate valve casing. Instead, the sample collection and filtration device 5020 can have a valve element 5050 moveably secured directly to the sample collection portion 5020.

Figure 25B:
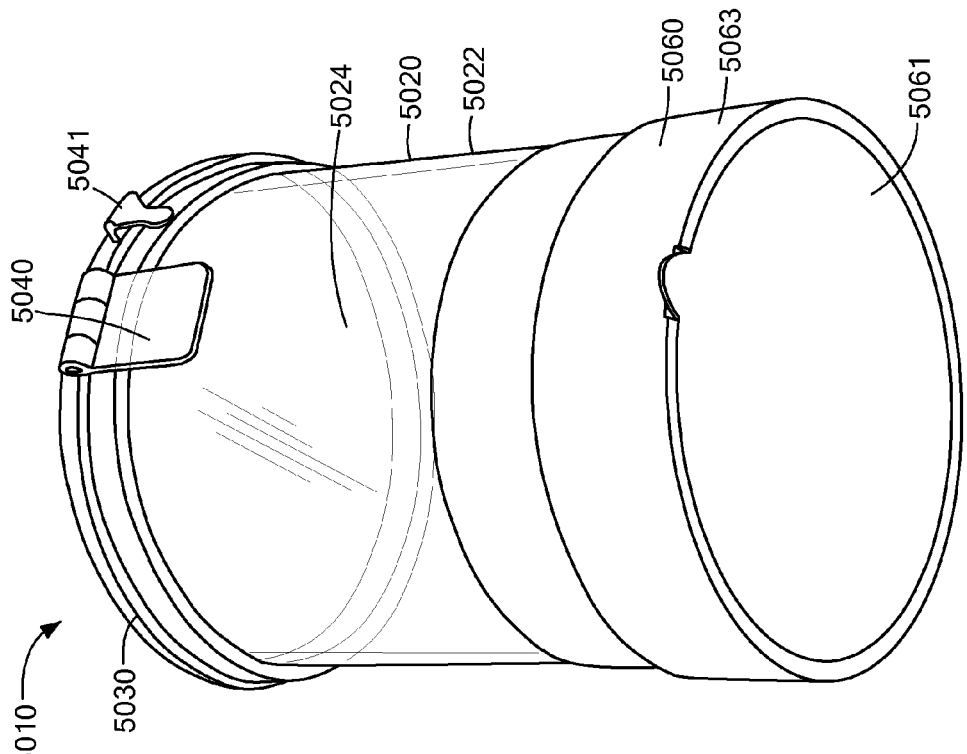
FIG. 25B schematically shows a bottom perspective view of the sample collection and filtration device shown in FIG. 25A, in accordance with illustrative embodiments of the present invention.
Figure 25A:
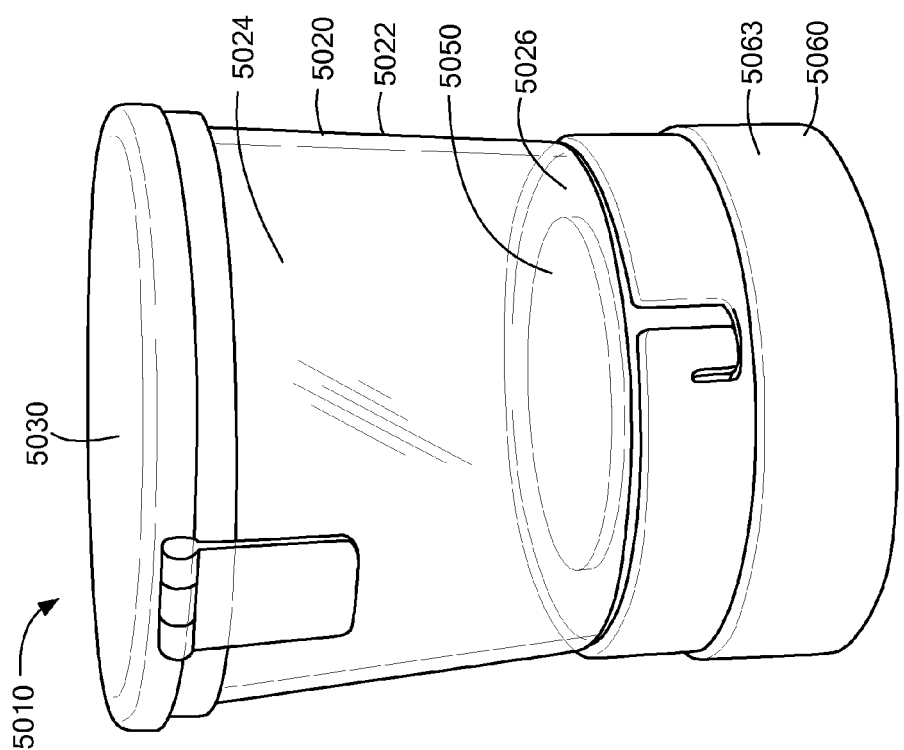
FIG. 25A schematically shows a side perspective view of a further embodiment of a sample collection and filtration device, in accordance with illustrative embodiments of the present invention.
Figure 25C:
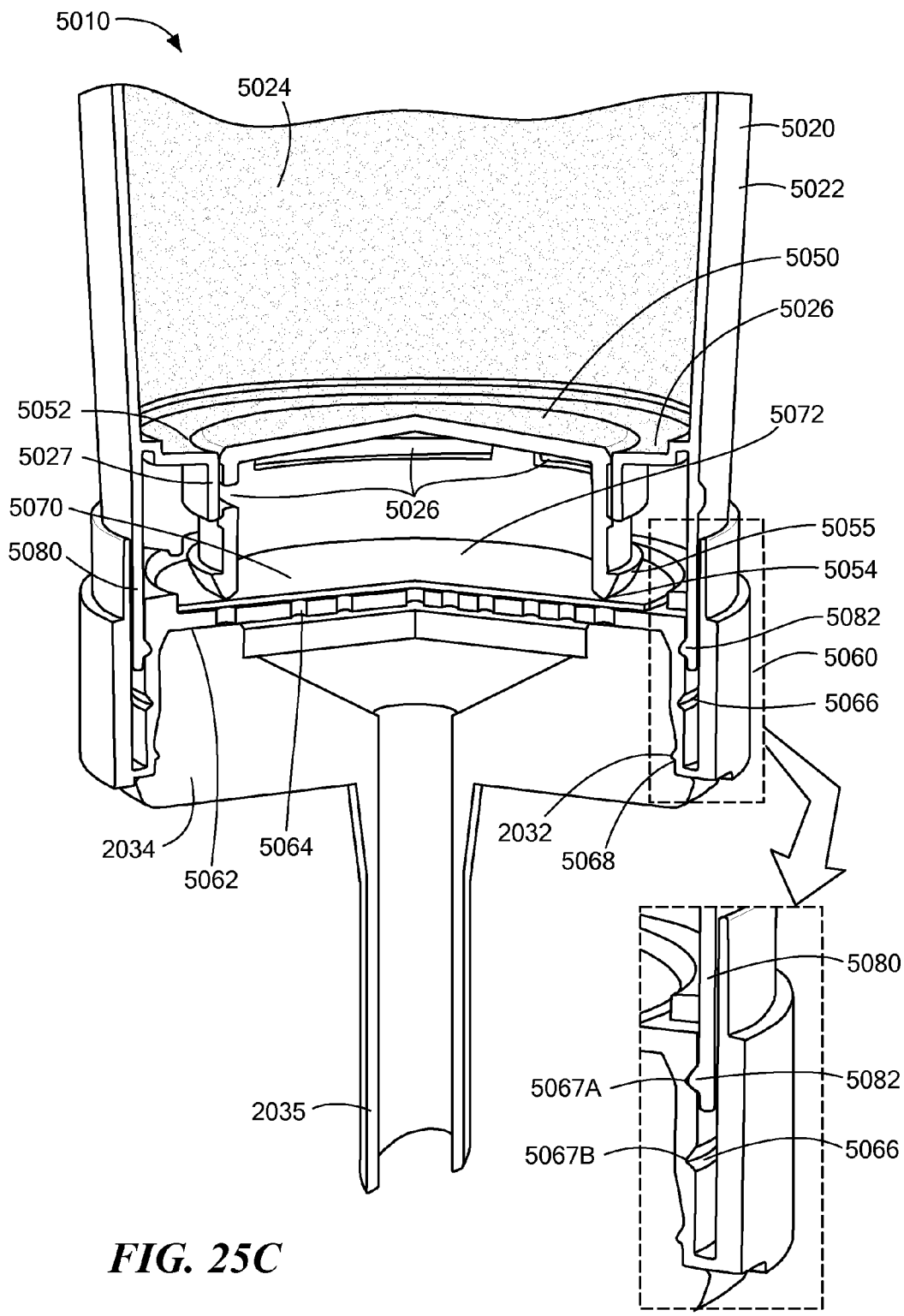
FIG. 25C schematically shows cross-sectional view of the sample collection and filtration device shown in FIG. 25A in the closed mode, in accordance with illustrative embodiments of the present invention.
Figure 25D:
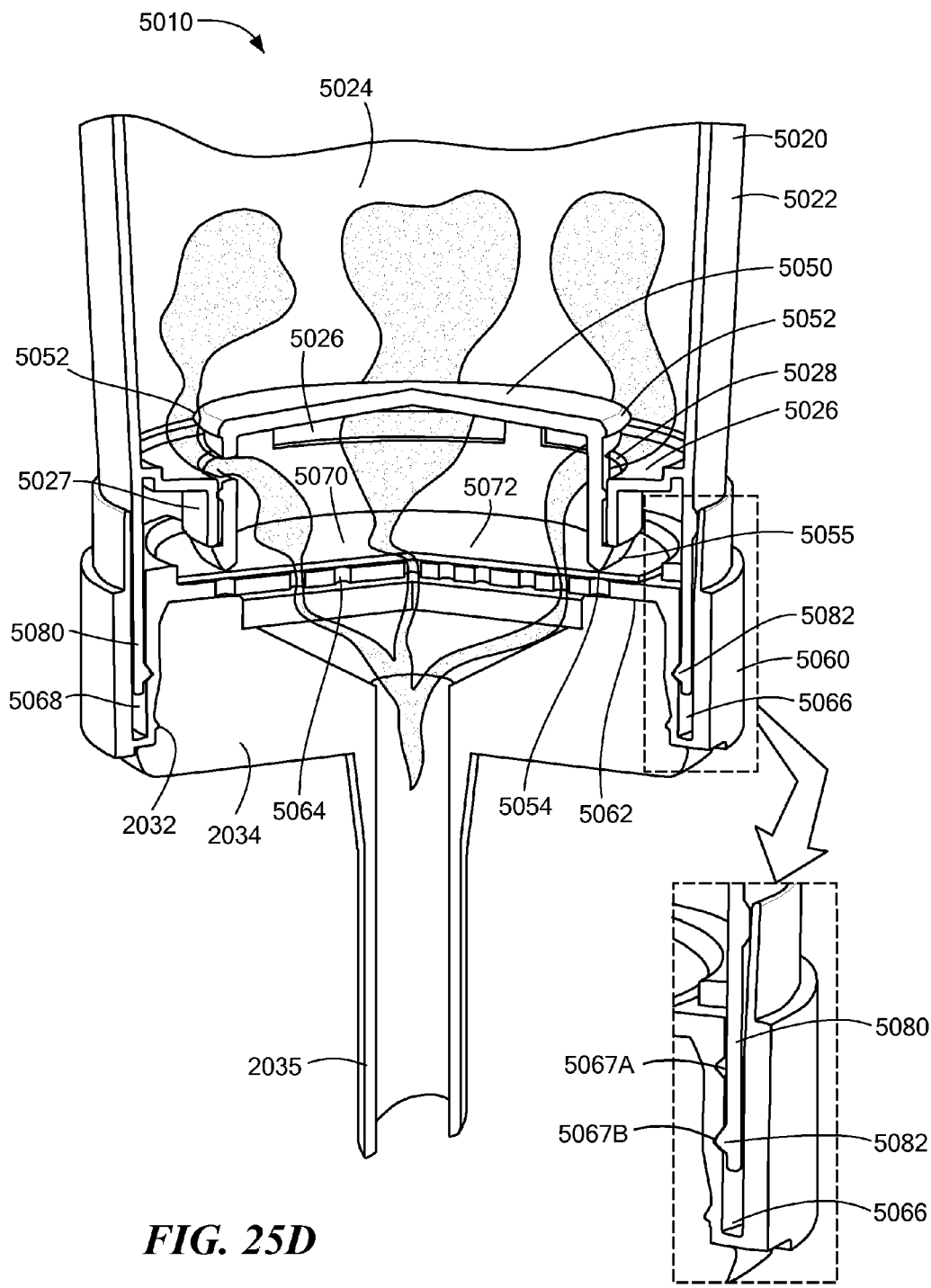
FIG. 25D schematically shows cross-sectional view of the sample collection and filtration device shown in FIG. 25A in the open mode, in accordance with illustrative embodiments of the present invention.
Figure 25E:
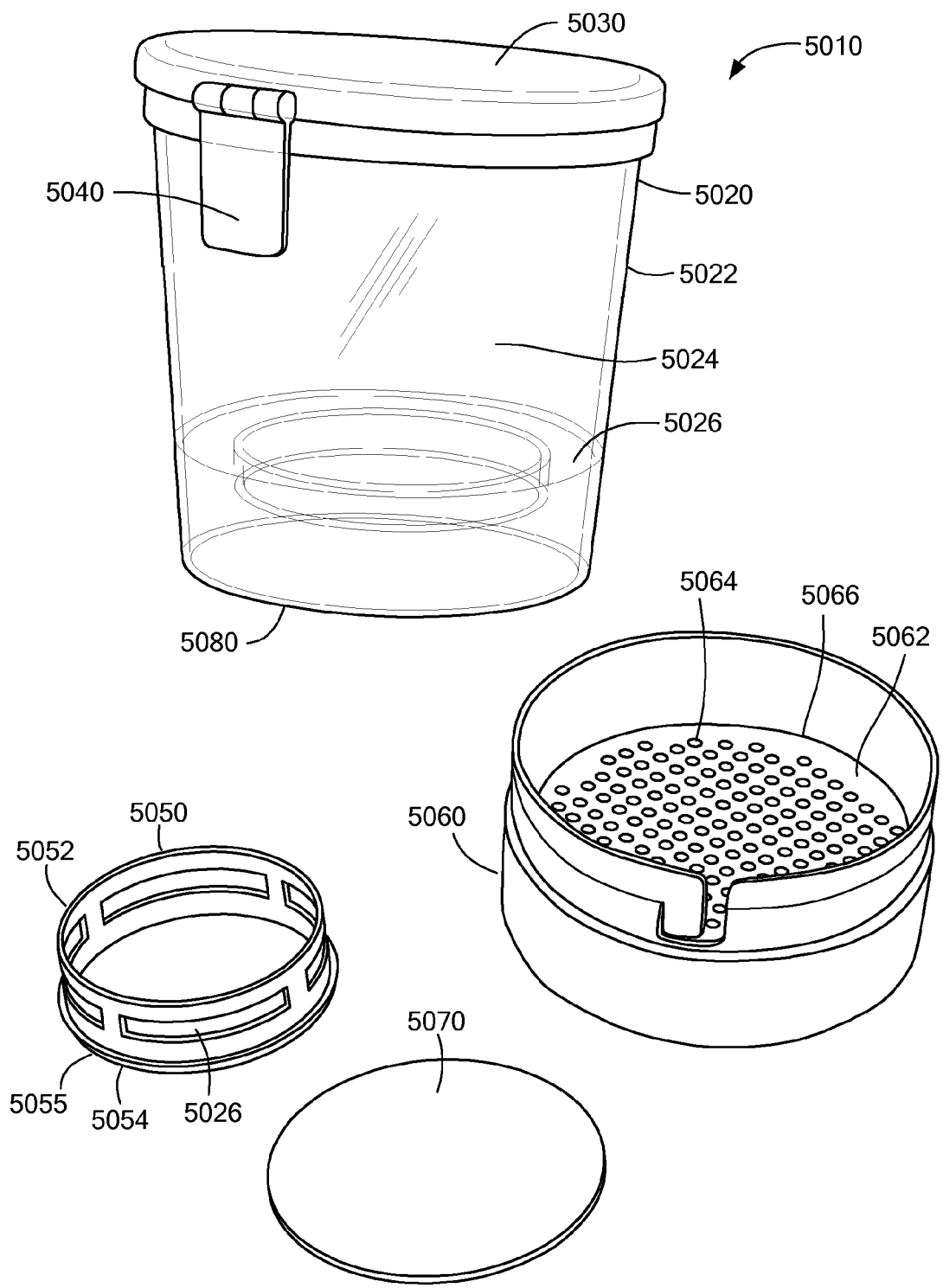
FIG. 25E schematically shows an exploded view of the sample collection and filtration device shown in FIG. 25A, in accordance with illustrative embodiments of the present invention.

For example, as best shown in FIGS. 25C and 25D, the valve element 5050 can extend through the bottom wall 5026 of the sample collection portion 5020 (e.g., through the fluid path/outlet 5027) and can be moveable within the fluid path/outlet 5027. In order to prevent leakage past the valve member 5050 when in the closed position (shown in FIG. 25C), the valve element 5050 can have an annular flange 5052, and the bottom wall 5027 can have a chamfered edge 5028 around the fluid path/outlet 5027 through the bottom wall 5027. When in the closed mode, the annular flange 5052 can sit within and create a seal against the chamfered edge 5028. Some embodiments may also include a seal member (e.g., an O-ring or a resilient material) on the flange 5052 and/or the chamfered edge to improve the seal. As discussed in greater detail below, when the valve member 5050 opens, it moves into the interior volume 5024 exposing a number of vents/passages 5026 through which the sample can flow.

The sample collection and filtration device 5010 can also have a coupling portion 5060 that can be secured to the vacuum base 2030 during filtration. The coupling portion 5060 can include a filter support surface 5062 that supports a filter membrane 5070. In order to allow the filtered sample to flow through the device 5010, the support surface 5062 can include a number of perforations 5064 through which the filtered sample can flow. The filter support surface 5062 also creates a barrier between the filter membrane 5070 and the vacuum base 2030 to prevent any bacteria on the vacuum base 2030 from contacting the filter membrane 5070.

In some embodiments, a bottom annular surface 5054 of the valve member 5050 can contact the top surface 5072 of the filter membrane 5070 and create a seal. In this manner, the filtration area of the filter membrane 5070 can be limited to the area directly under the valve member 5050 (e.g., the area inward from the annular surface 5045 of the valve member 5050). In such embodiments, the perforations 5064 may only be located beneath the filtration area of the filter 5070 (e.g., they may not extend all the way to the edge of the filter 5070). Furthermore, the seal between the annular surface 5054 of the valve member 5050 and the top surface 5072 of the filter membrane 5070 can prevent fluid from reaching the edge of the filter membrane 5070 and leaking past the membrane 5070. In order to preserve the sterility of the coupling portion 5060 and filter membrane 5070, the device 5010 can also have a removable seal 5061 that covers the bottom of the device.

As shown in FIGS. 25C and 25D, to facilitate the relative movement between the sample collection portion 5020 and the coupling portion 5060, the sample collection portion 5020 may have a skirt 5080 that resides within a recess 5066 in the coupling portion 5060. As the sample collection portion 5020 is pushed down, the skirt 5080 may slide within (e.g., downward) the recess 5066 to allow the relative movement between the sample collection portion 5020 and the coupling portion 5060. In order to lock the sample collection portion 5020 in place (e.g., in the closed or the open positions), the skirt 5080 can have a protrusion 5082 (or an annular ridge) that moves into and out of grooves 5067A/B as the sample container portion 5020 is pushed down. For example, when the valve 5050 is in the closed position (shown in FIG. 24C), the protrusion 5082 may reside within the top groove 5067A. As the sample collection portion 5020 is pushed down, the protrusion 5082 may move out of the top groove 5067A, slide downward within the recess 5066, and enter the bottom groove 5067B, locking the sample collection portion 5020 in the second (e.g., open) position.

The relative movement between the sample collection portion 5020 and the coupling portion 5060 opens and closes the valve member 5050 to allow or prevent fluid flow out the interior cavity 5024. To that end, as the technician pushes down on the sample collection portion 5020 (which causes the sample collection portion 5020 to move downward relative to the coupling portion 5060), the filter membrane 5070 and the filter support surface 5062 prevent equivalent downward/longitudinal movement of the valve member 5050, causing the valve member 5050 to move into the interior cavity 5024, and exposing the fluid passageways 5056 through valve member 5050. Once the valve member 5050 is open (e.g., the passageways 5056 are exposed), the sample is free to flow through the passageways and towards the filter membrane 5070.

Returning to FIG. 25B, some embodiments can also include a second tamper evident latch 5041 located on the top cover 5030 (or the sample collection portion 5020). This tamper evident latch 5041 can be closed and latched prior to packaging and/or sterilizing the sample collection and filtration device 5010 (e.g., prior to packaging it within the sterile bag). In this manner, the technician can be confident that the sample collection and filtration device (and particularly, the sample collection portion 5020) was not tampered with prior to collecting the sample. In such embodiments, the second tamper evident latch 5041 can be broken prior to collecting the sample so that the top cover 5030 can be opened.

It is important to note that some embodiments can have features that prevent the valve member 5050 from opening too far and becoming dislodged from the bottom wall 5026 and/or the fluid path/outlet 5027. For example, the annular surface 5054 can have a lip 5055 that engages the bottom of the fluid path/outlet 5027 when in the fully open position to prevent further movement of the valve member 5050 into the interior cavity 5024.

Figure 26:
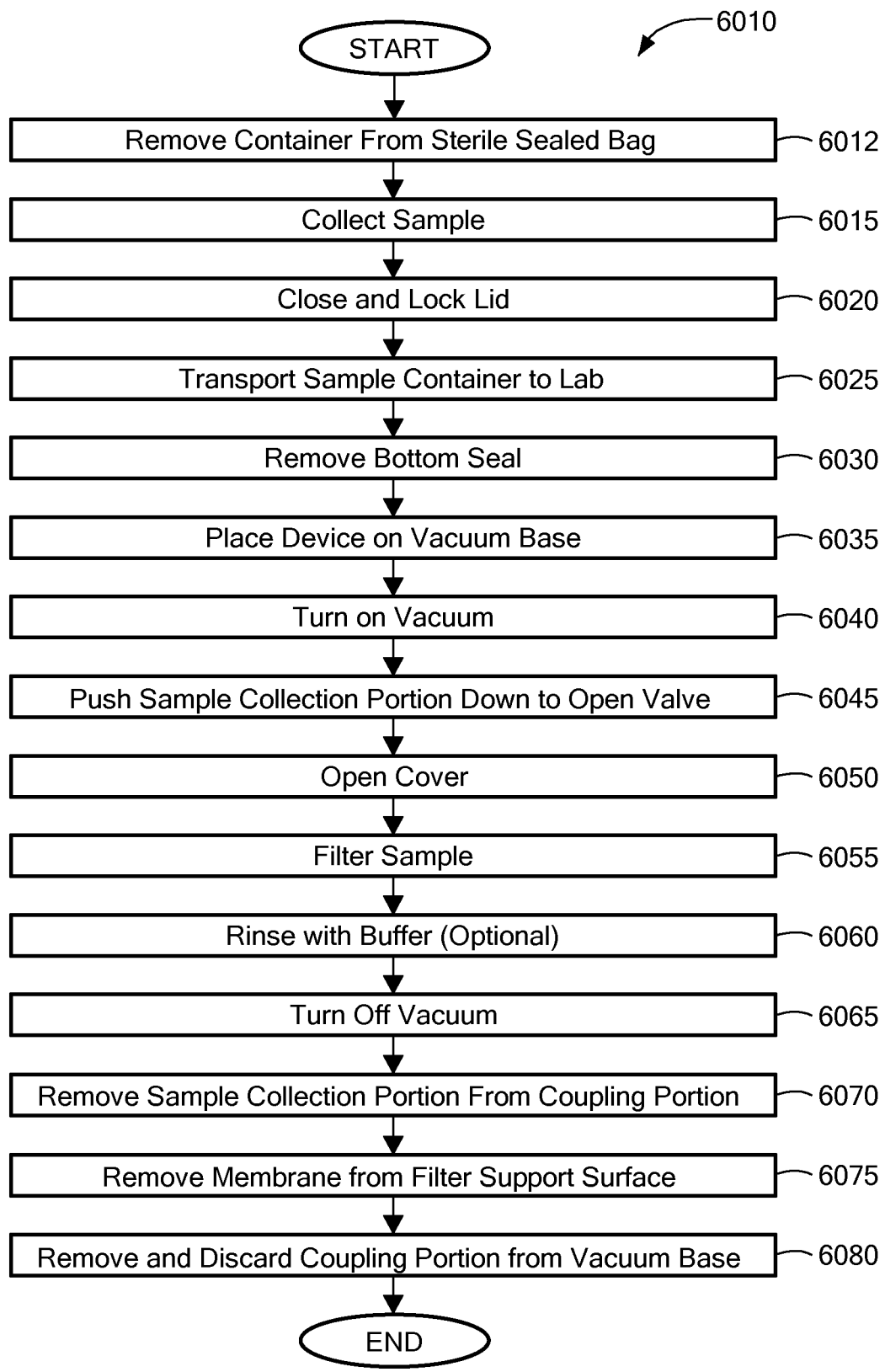
FIG. 26 shows a process of using the sample container shown in FIG. 25A in accordance with illustrative embodiments of the present invention.

FIG. 26 shows a process 6010 illustrating one use of the sample container and filtration apparatus 5010 shown in FIGS. 25A-25H. After removing the sample container 5010 from any packaging (e.g., a sterile sealed bag) (Step 6012)

and opening the top cap 5030, the user may then collect the sample within the sample collection portion 5020 (e.g., within the interior cavity 5024) (Step 6015), close and lock the top cap 5030 using the tamper evident latch (if equipped) (Step 6020), and transport the sample to the laboratory (Step 6025).

Once in the laboratory and the user/lab technician is ready to filter the sample, the user/technician can remove the seal 5061 from the bottom of the coupling portion 5060 (Step 6030) and place the sample container 5010 onto the vacuum base 2030 (Step 6035). As the sample container 5010 is placed onto the vacuum base 2030, the annular distally extending wall 5063 can extend over the vacuum base 2030 (or the vacuum adapter 2034) and the indent 2032 on the vacuum base 2030 can receive the protrusion 5068 on the annular wall 5063, locking the apparatus 5010 in place.

After locking the sample container 5010 to the base 2030, the user/technician may turn on the vacuum (Step 6040), and push the sample collection 5020 down to open the valve element 5050 (e.g., move it from the position shown in FIG. 25C to the position shown in FIG. 25D) and allow fluid flow through the vents/passages 5026 within the valve element 5050 and out of the sample collection portion 5020 (Step 6045). Once the valve is open (e.g., the vents/passageways 5026 are exposed to the interior volume 5024), the user/technician may open the top cap 5030 (and break the tamper evident latch if equipped) (Step 6050).

Once the top cap 5030 is opened and the vacuum is on, the vacuum applied to the sample container 5010 will cause the sample to be drawn from the interior cavity 5024, and through the filter membrane 5070 and perforations 5064 in the filter support surface 5062 (Step 6055). After filtration is complete, the user/technicians may optionally rinse the sample container 5010 (e.g., the interior cavity 5024) with a buffer solution (Step 6060) and then turn off the vacuum (Step 6065). The user/technician may then remove the sample collection portion 5020 from the coupling portion 5060 (e.g., by pulling them apart, causing the skirt 5080 to become dislodged from the recess 5066) (Step 6070), which exposes the filter membrane 5070. The technician may then remove the filter membrane 5070 from the vacuum base (Step 6075) for further processing, and remove the coupling portion 5060 from the vacuum base 2030 and discard it (Step 6080).

It is important to note that, although the embodiments discussed above are shown to have snap fit (e.g., protrusion/indent arrangements) connections between the various components (e.g., the sample collection portion, valve casing, coupling portion, etc.), other embodiments may use different coupling arrangements. For example, some embodiments may utilize threads and/or magnets to secure the various components together. Additionally, threads and/or magnets may be utilized to secure the sample collection and filtration devices to the vacuum base 2030.

Depending on the vacuum base 2030 utilized by the technician, some of the above described embodiments may be used in conjunction with a vacuum adapter 2034 (best shown in FIGS. 23A-23J). For example, if the vacuum base 2030 merely includes a vacuum port 2037 and a rubber stopper 2038, the vacuum adapter 2034 may be used to provide the necessary connection surface for the device. To that end, the vacuum adapter 2034 may include a main body 2035 with the protrusion/indent required to connect the device to the adapter 2034. Additionally, the adapter 2034 may include a spike 2036 that can either pierce through the rubber stopper 2038 or pass through a through-hole 2039 extending through the stopper 2038. The adapter 2034 may be re-usable and may be made from an autoclavable material (e.g., stainless steel) so that the adapter 2034 can be autoclaved/sterilized prior to use.

Although the above discussion discloses various exemplary embodiments of the invention, it should be apparent that those skilled in the art can make various modifications that will achieve some of the advantages of the invention without departing from the true scope of the invention.

What is claimed is:

1. A sample container and filtration apparatus comprising:
   a sample collection portion having at least one wall defining an interior volume of the sample container and a fluid path passing through a bottom wall;
   a valve casing moveably connected to the sample collection portion, the sample collection portion and valve casing being moveable relative to one another between a first position and a second position;
   a valve secured to and stationary with respect to the valve casing, the valve located within and closing the fluid path of the sample collection portion when the valve casing is in the first position and configured to move into the interior volume of the sample container to open the fluid path when the valve casing is in the second position;
   a vacuum base coupling portion located below the valve casing such that the valve casing is between the sample collection portion and the vacuum base, the vacuum base coupling portion including a filter membrane support surface; and
   a filter membrane supported by the filter membrane support surface, the filter membrane configured to filter a sample collected within the sample collection portion.

2. A sample container and filtering apparatus according to claim 1 further comprising a locking mechanism located between the sample container portion and the valve casing, the locking mechanism preventing the relative movement between the sample collection portion and the valve casing.

3. A sample container and filtering apparatus according to claim 2, wherein the locking mechanism includes a peel strip, the peel strip being removable from the sample container to allow the relative movement between the sample collection portion and the valve casing.

4. A sample container and filtering apparatus according to claim 3, wherein the peel strip include a peel tab.

5. A sample container and filtering apparatus according to claim 1, wherein the sample collection portion includes a skirt extending distally from the bottom surface of the sample collection portion.

6. A sample container and filtering apparatus according to claim 5, wherein the valve casing includes a proximally extending wall defining a recess within the valve casing, the skirt extending into the recess.

7. A sample container and filtering apparatus according to claim 6, wherein the proximally extending wall includes a plurality of protrusions extending inward from the proximally extending wall, the skirt including a plurality of indentations, the protrusions extending into the indentations to lock the sample collection portion to the valve casing.

8. A sample container and filtering apparatus according to claim 6, wherein the skirt includes a plurality of protrusions extending out from the skirt, the proximally extending wall including a plurality of indentations, the protrusions extending into the indentations to lock the sample collection portion to the valve casing.

9. A sample container and filtering apparatus according to claim 1, wherein the sample collection portion includes a cover with a tamper evident latch.

10. A sample container and filtering apparatus according to claim 1 further comprising a bottom cap configured to fit over a bottom of the vacuum base coupling portion and including a tamper evident latch.

11. A sample container and filtering apparatus according to claim 1, wherein the valve casing has an annular surface that contacts an upper surface of the filter membrane.

12. A sample container and filtering apparatus according to claim 11, wherein the annular surface seals against the upper surface of the filter membrane.

13. A sample container and filtering apparatus according to claim 1, wherein the vacuum base coupling portion includes an outlet downstream of the filter membrane and passing through the filter membrane support surface.

14. A sample container and filtering apparatus according to claim 1, wherein the filter membrane support surface includes a plurality of filter support ribs and a plurality of channels, the plurality of filter support ribs supporting the filter membrane, the plurality of channels configured to channel fluid passing through the filter to an outlet of the sample container and filtering apparatus.

15. A sample container and filtering apparatus according to claim 1, wherein the vacuum base coupling portion includes at least one protrusion configured to interact with a vacuum base to secure the sample container to the vacuum base.

16. A sample container and filtering apparatus according to claim 1, wherein the filter membrane is distal to the fluid path.

17. A sample container and filtering apparatus according to claim 1, wherein the sample collection portion and the valve casing are moveable relative to one another in a telescopic manner.

* * * * *